(12) United States Patent
Kim et al.

(10) Patent No.: US 8,771,844 B2
(45) Date of Patent: Jul. 8, 2014

(54) HETEROCYCLIC COMPOUND AND ORGANIC LIGHT-EMITTING DIODE AND FLAT DISPLAY DEVICE INCLUDING THE HETEROCYCLIC COMPOUND

(75) Inventors: Young-Kook Kim, Yongin (KR); Seok-Hwan Hwang, Yongin (KR); Hye-Jin Jung, Yongin (KR); Jin-O Lim, Yongin (KR); Sang-Hyun Han, Yongin (KR); Yoon-Hyun Kwak, Yongin (KR); Sun-Young Lee, Yongin (KR); Se-Jin Cho, Yongin (KR); Jong-Hyuk Lee, Yongin (KR); Sung-Chul Kim, Yongin (KR)

(73) Assignee: Samsung Display Co., Ltd., Yongin, Gyeonggi-Do (KR)

( * ) Notice: Subject to any disclaimer, the term of this patent is extended or adjusted under 35 U.S.C. 154(b) by 145 days.

(21) Appl. No.: 13/312,002

(22) Filed: Dec. 6, 2011

(65) Prior Publication Data

US 2012/0326135 A1 Dec. 27, 2012

(30) Foreign Application Priority Data

Jun. 22, 2011 (KR) .................. 10-2011-0060807

(51) Int. Cl.
  *H01L 51/54* (2006.01)
(52) U.S. Cl.
  USPC ........... 428/690; 428/917; 313/504; 313/505; 313/506; 257/40; 257/E51.05; 257/51.026; 257/51.032; 548/304.1; 548/418; 548/440; 548/444; 546/18; 546/79; 546/81; 546/101; 585/27
(58) Field of Classification Search
  USPC .................. 428/690, 917; 313/504, 505, 506; 257/40, E51.05, E51.026, E51.032; 548/418, 440, 304.1, 444; 546/18, 79, 546/81, 101; 585/27
  See application file for complete search history.

(56) References Cited

U.S. PATENT DOCUMENTS

| | | | |
|---|---|---|---|
| 5,635,308 | A | 6/1997 | Inoue et al. |
| 5,645,948 | A | 7/1997 | Shi et al. |
| 5,972,247 | A | 10/1999 | Shi et al. |
| 6,465,115 | B2 | 10/2002 | Shi et al. |
| 6,596,415 | B2 | 7/2003 | Shi et al. |
| 2007/0069203 | A1* | 3/2007 | Lee et al. .................. 257/40 |
| 2008/0203905 | A1 | 8/2008 | Je et al. |
| 2011/0084256 | A1 | 4/2011 | Kim et al. |
| 2011/0215308 | A1* | 9/2011 | Im et al. .................. 257/40 |

FOREIGN PATENT DOCUMENTS

| | | | |
|---|---|---|---|
| JP | 8-12600 A | | 1/1996 |
| JP | 2000-003782 A | | 1/2000 |
| JP | 2006-066580 A | | 3/2006 |
| JP | 2008-078362 A | | 4/2008 |
| KR | 10-2010-0106014 A | | 10/2010 |
| KR | 10-2010-0108924 A | | 10/2010 |
| KR | 10-2011-0039108 A | | 4/2011 |
| KR | 2011041726 | * | 4/2011 |
| WO | WO 2010132953 | * | 11/2010 |

OTHER PUBLICATIONS

Tang, C.W., et al., "Organic electroluminescent diodes," *Applied Physics Letters*, vol. 51, Issue 12, Sep. 21, 1987, pp. 913-915.

Adachi, Chihaya, et al., "Confinement of charge carriers and molecular excitons within 5-nm-thick emitter layer in organic electroluminescent devices with a double heterostructure," *Applied Physics Letters*, vol. 57, Issue 6, Aug. 6, 1990, pp. 531-533.

Sakamoto, Youichi, et al., "Synthesis, Characterization, and Electron-Transport Property of Perfluorinated Phenylene Dendrimers," *Journal of the American Chemical Society*, vol. 122, 2000, pp. 1832-1833.

Yamaguchi, et al.; Diphenylamino-Substituted 2,5-Diarylsiloles for Single-Layer Organic Electoluminescent Devices; Chemistry Letters; 2001; Chemical Society of Japan.

* cited by examiner

*Primary Examiner* — Gregory Clark
(74) *Attorney, Agent, or Firm* — Lee & Morse, P.C.

(57) ABSTRACT
A heterocyclic compound, an organic light-emitting diode, and a flat display device, the heterocyclic compound being represented by Formula 1, below:
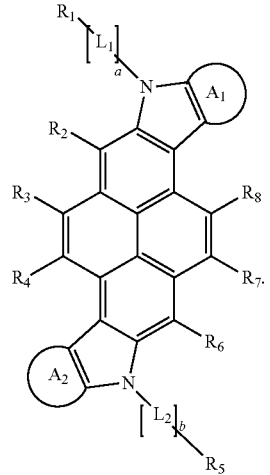
<Formula 1>
23 Claims, 1 Drawing Sheet

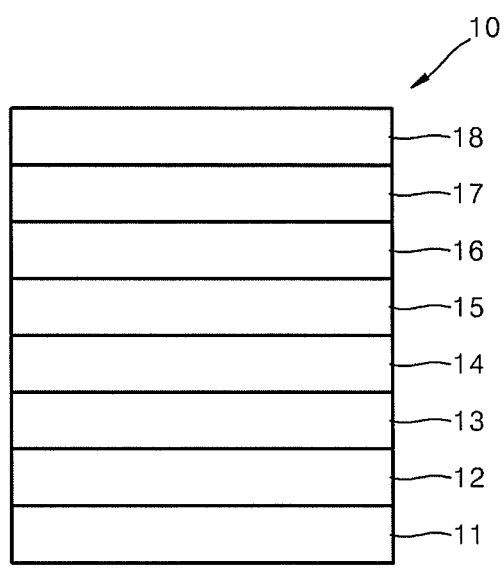

HETEROCYCLIC COMPOUND AND ORGANIC LIGHT-EMITTING DIODE AND FLAT DISPLAY DEVICE INCLUDING THE HETEROCYCLIC COMPOUND

CROSS-REFERENCE TO RELATED PATENT APPLICATION

This application claims the benefit of Korean Patent Application No. 10-2011-0060807, filed on Jun. 22, 2011, in the Korean Intellectual Property Office, the disclosure of which is incorporated herein in its entirety by reference.

BACKGROUND

1. Field

Embodiments relate to a heterocyclic compound, and an organic light-emitting diode and a flat display device including the heterocyclic compound, and more particularly, to a heterocyclic compound that is suitable for use as a light-emitting material or electron transporting material included in an organic light-emitting diode, an organic light-emitting diode including the heterocyclic compound, and a flat display device including the organic light-emitting diode. The organic light-emitting diode including an organic layer including the heterocyclic compound has a low driving voltage, high luminescence efficiency, and long lifetime.

2. Description of the Related Art

Organic light emitting diodes are self-emission devices that have a wide viewing angle, a high contrast ratio, a short response time, and excellent brightness, driving voltage, and response speed characteristics, thus enabling the generation of multi-color images.

In an organic light-emitting diode, an anode may be formed on a substrate, and a hole transport layer, an emission layer, an electron transport layer, and a cathode may be sequentially formed in this stated order on the anode. In this regard, the hole transport layer, the emission layer, and the electron transport layer may be organic films including organic compounds. When a voltage is applied between the anode and the cathode, holes injected from the anode pass the hole transport layer to the emission layer, and electrons injected from the cathode pass the electron transport layer to the emission layer. The holes and electrons, which are carriers, are recombined in the emission layer to generate excitons, which then change from an excited state to a ground state, thereby generating light.

An emission layer material of an organic light-emitting diode may include anthracene derivatives. An electron transport material may include $Alq_3$, TBPi, PBD, PF-6P, PyPySPyPy, etc. An organic light-emitting diode may use a 2 or 3 equivalent amount of a compound of phenyl anthracene. However, a device using the 2 or 3 equivalent amount of the compound of phenyl anthracene may have two or three anthracenes covalently linked. Thus, an energy gap may be narrow and color purity of blue light emission may be low. Also, the 2 or 3 equivalent amount of the compound of phenyl anthracene may be oxidized and thus, purification thereof may be difficult. Accordingly, organic light-emitting diodes using either an anthracene compound in which naphthalene is substituted at sites 1 and 9 of an anthracene group or a diphenylanthracene compound in which an aryl group is substituted at an m-site of a phenyl group may be used. However, such organic light-emitting diodes may have low luminescence efficiency. Also, an organic light-emitting device may use a monoanthracene derivative substituted with a naphthalene. However, such an organic light-emitting diode may not be practical due to its low luminescence efficiency of about 1 cd/A. Also, an organic light-emitting diode may include a compound having the structure of phenyl anthracene. However, the compound may be substituted with an aryl group at an m-site thereof. Thus, the compound may have a luminescence efficiency as low as about 2 cd/A, although its heat resistance is high.

SUMMARY

The embodiments relate to a heterocyclic compound having a novel structure, and an organic light-emitting diode and a flat display device including the heterocyclic compound, wherein the organic light-emitting diode and the flat display device have a low driving voltage, high luminescence efficiency, and long lifetime due to the inclusion of the heterocyclic compound.

According to an aspect of the embodiments, there is provided a heterocyclic compound represented by Formula 1 below:

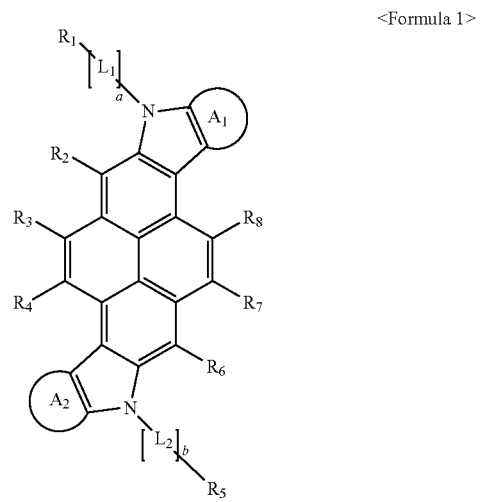

<Formula 1> wherein $A_1$ and $A_2$ are each independently a substituted or unsubstituted fused pyridine cycle, $R_1$ to $R_8$ are each independently a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cyclo alkyl group, a substituted or unsubstituted $C_3$-$C_{30}$ cyclo alkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_3$-$C_{30}$ hetero aryl group, and a group represented by $N(Q_1)(Q_2)$ wherein $Q_1$, and $Q_2$ are each independently a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cyclo alkyl group, a substituted or unsubstituted $C_3$-$C_{30}$ cyclo alkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, or a substituted or unsubstituted $C_3$-$C_{30}$ hetero aryl group, and $L_1$ and $L_2$ are each independently a substituted or unsubstituted $C_6$-$C_{30}$ arylene group, or a substituted or unsubstituted $C_3$-$C_{30}$ heteroarylene group, and a and b are each independently an integer of 0 to 3.

According to another aspect of the embodiments, there is provided an organic light-emitting diode including: a first electrode; a second electrode facing the first electrode; and a first layer interposed between the first electrode and the second electrode, wherein the first layer includes the heterocyclic compound alone or in a mixed form with other materials.

According to another aspect of the embodiments, there is provided a flat display device including: a transistor comprising a source, a drain, a gate, and an active layer; and the organic light-emitting diode, wherein the source or the drain is electrically connected to the first electrode of the organic light-emitting diode.

BRIEF DESCRIPTION OF THE DRAWINGS

The embodiments will become apparent by describing in detail exemplary embodiments thereof with reference to FIG. 1 which illustrates a schematic view of an organic light-emitting diode according to an embodiment.

DETAILED DESCRIPTION

An embodiment provides a heterocyclic compound represented by Formula 1:

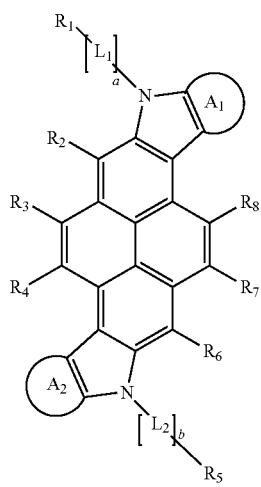

<Formula 1>

In Formula 1, $A_1$ and $A_2$ may each independently be a substituted or unsubstituted fused pyridine cycle. For example, the heterocyclic compound represented by Formula 1 may include two or more pyridine compounds symmetrically fused to a back bone of Formula 1. The fused pyridine cycles may be identical to or different from each other, and among hydrogen atoms that constitute the fused pyridine groups, one or more hydrogen atoms may be substituted with substituents or unsubstituted. Due to the inclusion of the symmetric pyridine cycles, the heterocyclic compound represented by Formula 1 has a high and stable glass transition temperature or melting point.

$A_1$ and $A_2$ may each independently be a group represented by one of Formulae 2A to 2D below, but is not limited thereto:

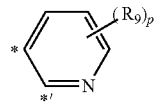

<Formula 2A>

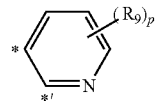

<Formula 2B>

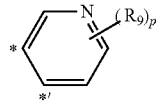

<Formula 2C>

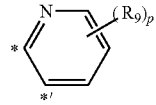

<Formula 2D>

In the above Formulae, $R_9$ may independently be a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cyclo alkyl group, a substituted or unsubstituted $C_3$-$C_{30}$ cyclo alkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_3$-$C_{30}$ hetero aryl group, or a group represented by $N(Q_3)(Q_4)$ wherein $Q_3$ and $Q_4$ are each independently a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cyclo alkyl group, a substituted or unsubstituted $C_3$-$C_{30}$ cyclo alkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, or a substituted or unsubstituted $C_3$-$C_{30}$ hetero aryl group.

Examples of $R_9$ may include a hydrogen atom, a deuterium atom, a halogen atom, a hydroxyl group, a cyano group, an amino group, a nitro group, a carboxyl group, a methyl group, an ethyl group, a propyl group, a butyl group, a pentyl group, a phenyl group, a non-phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, a phenanthridinyl group, a phenanthrollinyl group, an anthryl group, a fluorantenyl group, a triphenylenyl group, a pyrenyl group, a chricenyl group, a naphthacenyl group, a pycenyl group, a perylenyl group, a pentaphenyl group, a hexacenyl group, a pyrrolyl group, an imidazolyl group, a benzoimidazolyl group, a pyrazolyl group, a pyridinyl group, an imidazopyridinyl group, a pyrazinyl group, a pyrimidinyl group, an imidazopyrimidinyl group, a pyridazinyl group, an indolyl group, an isoindolyl group, a pyrido indolyl group, an indazolyl group, a purinyl group, a quinolinyl group, a benzoquinolinyl group, a phthalazinyl group, a naphthyridinyl group, a quinoxalinyl group, a quinazolinyl group, a carbazolyl group, a phenazinyl group, a puranyl group, a benzopuranyl group, a dibenzopuranyl group, a thiophenyl group, a benzothiophenyl group, a dibenzothiophenyl group, a thiazolyl group, an isothiazolyl group, a benzothiazolyl group, an oxazolyl group, a benzooxazolyl group, an isooxazolyl group, an oxadiazolyl group, a triazolyl group, a triazinyl group, a tetrazolyl group, etc.

Also, a plurality of $R_9$ may be identical to or different from each other, p may be an integer from 1 to 3, and * and *' may each represent a site that is to be fused to the back bond of Formula 1.

In an implementation, $A_1$ may be a group represented by one of Formulae 3AA to 3BB below:

<Formula 3AA>

<Formula 3AB>

<Formula 3AC>

<Formula 3AD>

<Formula 3AE>

<Formula 3AF>

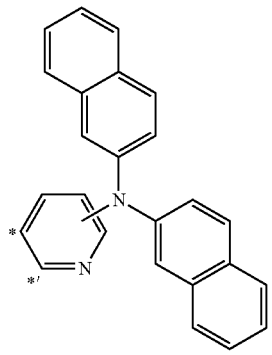

<Formula 3AG>

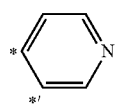

<Formula 3AH>

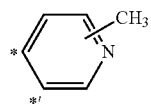

<Formula 3AI>

<Formula 3AJ>

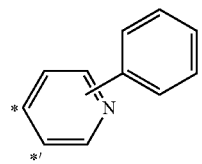

<Formula 3AK>

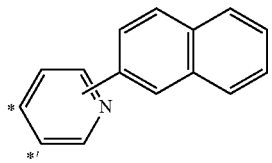

<Formula 3AL>

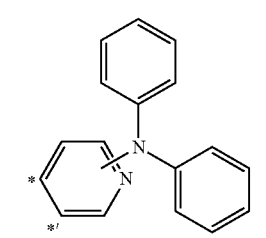

<Formula 3AM>

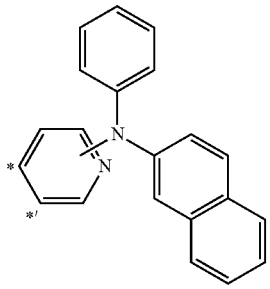

<Formula 3AN>

<Formula 3AO>

<Formula 3AP>

<Formula 3AQ>

<Formula 3AR>

<Formula 3AS>

<Formula 3AT>

<Formula 3AU>

<Formula 3AV>

<Formula 3AW>

<Formula 3AX>

<Formula 3AY>

<Formula 3AZ>

<Formula 3BA>

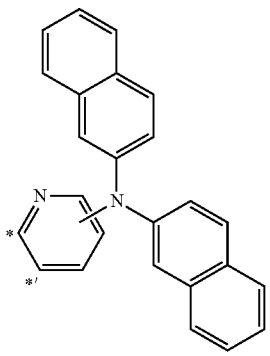

<Formula 3BB>

In the above Formulae, * and *' each represent a site that is to be fused to the back bond of Formula 1.

$R_1$ to $R_8$ in Formula 1 may each independently be a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cyclo alkyl group, a substituted or unsubstituted $C_3$-$C_{30}$ cyclo alkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_3$-$C_{30}$ hetero aryl group, or a group represented by $N(Q_1)(Q_2)$ wherein $Q_1$, and $Q_2$ are each independently a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cyclo alkyl group, a substituted or unsubstituted $C_3$-$C_{30}$ cyclo alkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, or a substituted or unsubstituted $C_3$-$C_{30}$ hetero aryl group.

For example, $R_1$ to $R_8$ may each independently be a hydrogen atom, a deuterium atom, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted nonphenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted phenanthridinyl group, a substituted or unsubstituted phenanthrollinyl group, a substituted or unsubstituted anthryl group, a substituted or unsubstituted fluorantenyl group, a substituted or unsubstituted triphenylenyl group, a substituted or unsubstituted pyrenyl group, a substituted or unsubstituted chricenyl group, a substituted or unsubstituted naphthacenyl group, a substituted or unsubstituted pycenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted benzoimidazolyl group, a substituted or unsubstituted pyrazolyl group, a substituted or unsubstituted pyridinyl group, a substituted or unsubstituted imidazopyridinyl group, a substituted or unsubstituted pyrazinyl group, a substituted or unsubstituted pyrimidinyl group, a substituted or unsubstituted imidazopyrimidinyl group, a substituted or unsubstituted pyridazinyl group, a substituted or unsubstituted indolyl group, a substituted or unsubstituted isoindolyl group, a substituted or unsubstituted pyrido indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthallazinyl group, a substituted or unsubstituted naphthyridinyl group, a substituted or unsubstituted quinoxalinyl group, a substituted or unsubstituted quinazolinyl group, a substituted or unsubstituted carbazolyl group, a substituted or unsubstituted phenazinyl group, a substituted or unsubstituted puranyl group, a substituted or unsubstituted benzopuranyl group, a substituted or unsubstituted dibenzopuranyl group, a substituted or unsubstituted thiophenyl group, a substituted or unsubstituted benzothiophenyl group, a substituted or unsubstituted dibenzothiophenyl group, a substituted or unsubstituted thiazolyl group, a substituted or unsubstituted isothiazolyl group, a substituted or unsubstituted benzothiazolyl group, a substituted or unsubstituted oxazolyl group, a substituted or unsubstituted benzooxazolyl group, a substituted or unsubstituted isooxazolyl group, a substituted or unsubstituted oxadiazolyl group, a substituted or unsubstituted triazolyl group, a substituted or unsubstituted triazinyl group, a substituted or unsubstituted tetrazolyl group, or a group represented by $N(Q_1)(Q_2)$ wherein $Q_1$, and $Q_2$ are each independently a hydrogen atom, a deuterium atom, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted anthryl group, a substituted or unsubstituted fluorenyl group, a substituted or unsubstituted carbazolyl group, or a substituted or unsubstituted pyridinyl group, but are not limited thereto.

In an implementation, $R_1$ to $R_8$ may each independently be a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted naphthyl group, a substituted or unsubstituted fluorenyl group, a substituted or unsubstituted phenanthrenyl group, a substituted or unsubstituted anthryl group, a substituted or unsubstituted triphenylenyl group, a substituted or unsubstituted pyrenyl group, a substituted or unsubstituted imidazolyl group, a substituted or unsubstituted benzoimidazolyl group, a substituted or unsubstituted pyridinyl group, a substituted or unsubstituted imidazopyridinyl group, a substituted or unsubstituted pyrimidinyl group, a substituted or unsubstituted imidazopyrimidinyl group, a substituted or unsubstituted indolyl group, a substituted or unsubstituted pyrido indolyl group, a substituted or unsubstituted carbazolyl group, a substituted or unsubstituted puranyl group, a substituted or unsubstituted benzopuranyl group, a substituted or unsubstituted dibenzopuranyl group, a substituted or unsubstituted thiophenyl group, a substituted or unsubstituted benzothiophenyl group, a substituted or unsubstituted dibenzothiophenyl group, a substituted or unsubstituted benzothiazolyl group, a substituted or unsubstituted benzooxazolyl group, a substituted or unsubstituted oxadiazolyl group, a substituted or unsubstituted triazinyl group, and a group represented by $N(Q_1)(Q_2)$ wherein $Q_1$ and $Q_2$ are each independently a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted naphthyl group, a substituted or unsubstituted fluorenyl group, a substituted or unsubstituted carbazolyl group, or a substituted or unsubstituted pyridinyl group.

$R_1$ and $R_5$ in Formula 1, like $A_1$, may affect characteristics of the heterocyclic compound. $R_1$ and $R_5$ in Formula 1 may each independently be a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted naphthyl group, a substituted or unsubstituted fluorenyl group, a substituted or unsubstituted phenanthrenyl group, a substituted or unsubstituted anthryl group, a substituted or unsubstituted triphenylenyl group, a substituted or unsubstituted pyrenyl group, a substituted or unsubstituted imidazolyl group, a substituted or unsubstituted benzoimidazolyl group, a substituted or unsubstituted pyridinyl group, a substituted or unsubstituted imidazopyridinyl group, a substituted or unsubstituted pyrimidinyl group, a substituted or unsubstituted imidazopyrimidinyl group, a substituted or unsubstituted indolyl group, a substituted or unsubstituted pyrido indolyl group, a substituted or unsubstituted carbazolyl group, a substituted or unsubstituted puranyl group, a substituted or unsubstituted benzopuranyl group, a substituted or unsubstituted dibenzopuranyl group, a substituted or unsubstituted thiophenyl group, a substituted or unsubstituted benzothiophenyl group, a substituted or unsubstituted dibenzothiophenyl group, a substituted or unsubstituted benzothiazolyl group, a substituted or unsubstituted benzooxazolyl group, a substituted or unsubstituted oxadiazolyl group, a substituted or unsubstituted triazinyl group, or a group represented by $N(Q_1)(Q_2)$ wherein $Q_1$, and $Q_2$ are each independently a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted naphthyl group, a substituted or unsubstituted fluorenyl group, a substituted or unsubstituted carbazolyl group, or a substituted or unsubstituted pyridinyl group. In this regard, $R_2$, $R_3$, $R_4$, $R_6$, $R_7$, and $R_8$ may each independently be a hydrogen atom, a deuterium atom, a halogen atom, a substituted or unsubstituted methyl group, a substituted or unsubstituted ethyl group, a substituted or unsubstituted propyl group, a substituted or unsubstituted butyl group, or a substituted or unsubstituted pentyl.

In an implementation, $R_1$ and $R_5$ may each independently be a hydrogen atom, a deuterium atom, a halogen atom, a substituted or unsubstituted methyl group, a substituted or unsubstituted ethyl group, a substituted or unsubstituted propyl group, a substituted or unsubstituted isobutyl group, or one of the groups represented by Formulae 4AA to 4BK, below, and of $R_2$, $R_3$, $R_4$, $R_6$, $R_7$, and $R_8$ may be hydrogen atoms:

<Formula 4AA>

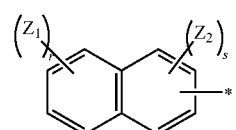
<Formula 4AB>

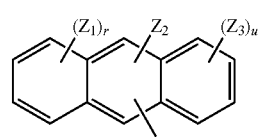
<Formula 4AC>

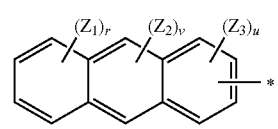
<Formula 4AD>

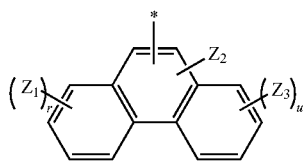
<Formula 4AE>

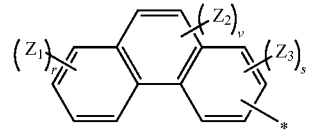
<Formula 4AF>

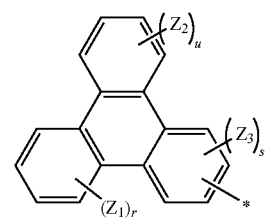
<Formula 4AG>

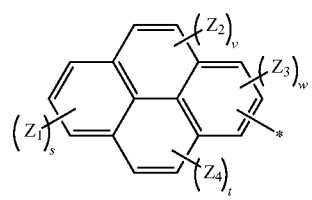
<Formula 4AH>

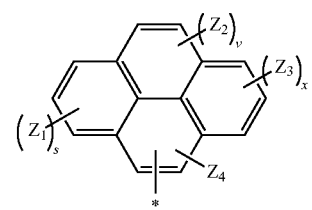
<Formula 4AI>

<Formula 4AJ>
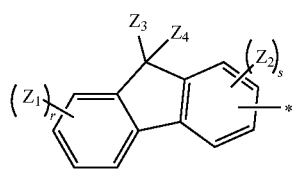
<Formula 4AK>
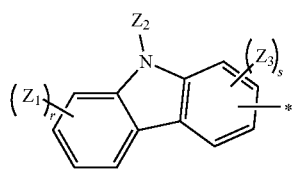
<Formula 4AL>
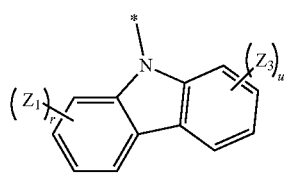
<Formula 4AM>
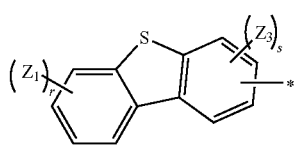
<Formula 4AN>
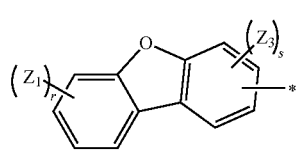
<Formula 4AO>
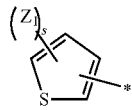
<Formula 4AP>
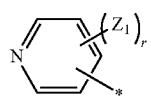
<Formula 4AQ>
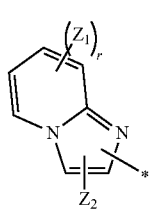
<Formula 4AR>
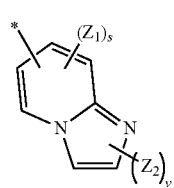
<Formula 4AS>
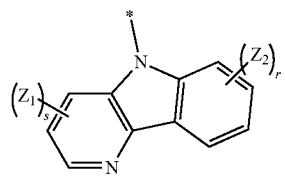
<Formula 4AT>
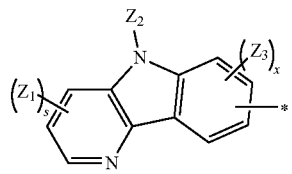
<Formula 4AU>
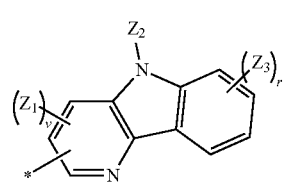
<Formula 4AV>
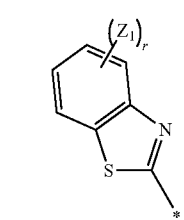
<Formula 4AW>
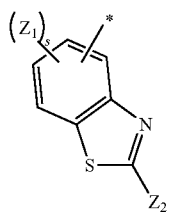
<Formula 4AX>
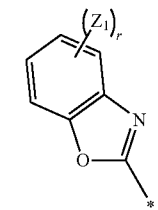
<Formula 4AY>
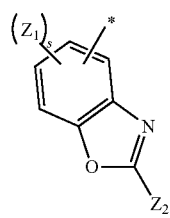
<Formula 4AZ>

<Formula 4BA>
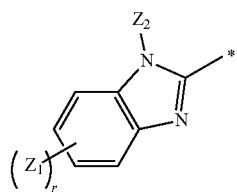

<Formula 4BB>
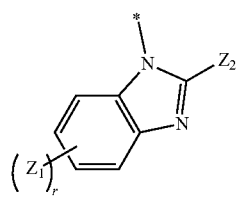

<Formula 4BC>
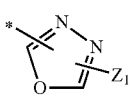

<Formula 4BD>
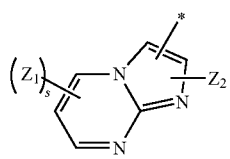

<Formula 4BE>
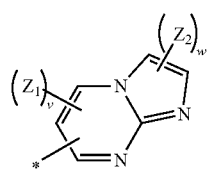

<Formula 4BF>
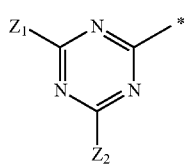

<Formula 4BG>
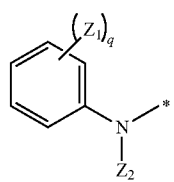

<Formula 4BH>
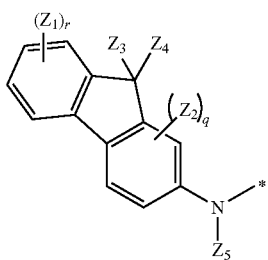

<Formula 4BI>
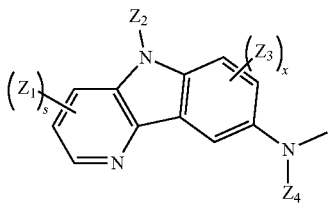

<Formula 4BJ>
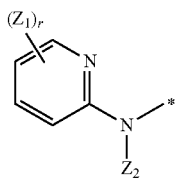

<Formula 4BK>
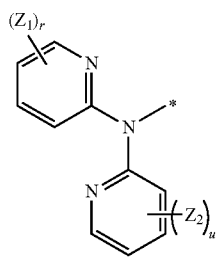

In the above Formulae, $Z_1$, $Z_2$, $Z_3$, $Z_4$, and $Z_5$ may each independently be a hydrogen atom, a deuterium atom, a halogen atom, a hydroxy group, a cyano group, a trifluoromethyl group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, a substituted or unsubstituted anthryl group, or a substituted or unsubstituted pyridinyl group, a plurality of each of $Z_1$, $Z_2$, $Z_3$, $Z_4$, and $Z_5$ may be identical to or different from each other, q may be an integer of 1 to 5, r and u may each independently be an integer of 1 to 4, s and x may each independently be an integer of 1 to 3, v may an integer of 1 or 2, and * may represent a binding site.

$L_1$, and $L_2$ in Formula 1 may be divalent linkers, and may each independently be a substituted or unsubstituted $C_6$-$C_{30}$ arylene group or a substituted or unsubstituted $C_3$-$C_{30}$ heteroarylene group. a and b may each represent a number of divalent linkers connected in series and may each independently be an integer of 0 to 3.

In an implementation, $L_1$ and $L_2$ may each independently be a substituted or unsubstituted phenylene group, a substituted or unsubstituted naphthylene group, a substituted or unsubstituted anthrylene group, a substituted or unsubstituted phenanthrenylene group, a substituted or unsubstituted pyrenylene group, a substituted or unsubstituted chrysenylene group, a substituted or unsubstituted perylenylene group, a substituted or unsubstituted fluorenylene group, a substituted or unsubstituted spiro-fluorenyl group, a substituted or unsubstituted carbazolylene group, a substituted or unsubstituted pyridinylene group, a substituted or unsubstituted pyrimidinylene group, or a substituted or unsubstituted oxadiazolylene group.

In an implementation, $L_1$ and $L_2$ may each independently be a group represented by one of Formulae 5A to 5I, below, but are not limited thereto:

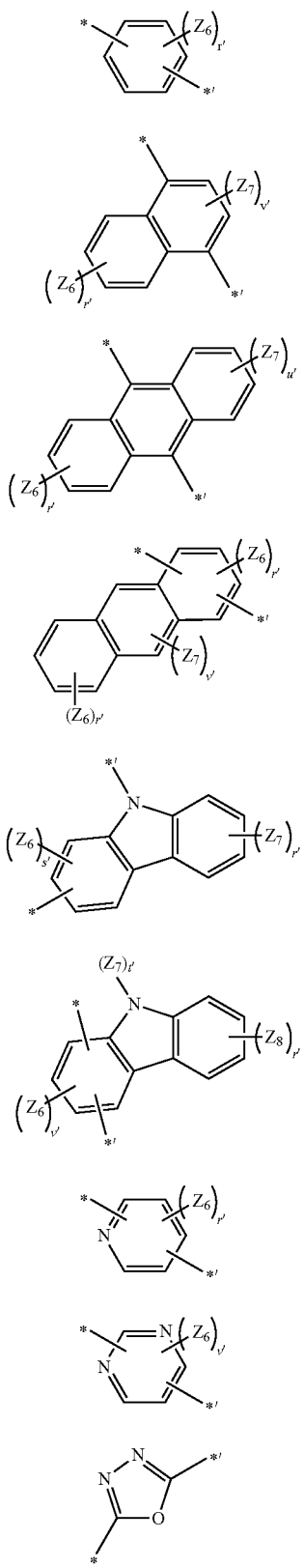

<Formula 5A>
<Formula 5B>
<Formula 5C>
<Formula 5D>
<Formula 5E>
<Formula 5F>
<Formula 5G>
<Formula 5H>
<Formula 5I>

In the above Formulae, $Z_6$, $Z_7$, and $Z_8$ may each independently be a hydrogen atom, a deuterium atom, a halogen atom, a substituted or unsubstituted methyl group, a substituted or unsubstituted ethyl group, a substituted or unsubstituted propyl group, a substituted or unsubstituted butyl group, or a substituted or unsubstituted phenyl, and a plurality of each of $Z_6$, $Z_7$, and $Z_8$ may be identical to or different from each other. Also, r' and u' may each independently be an integer of 1 to 4, s' may be an integer of 1 to 3, v' and y' may each independently be an integer of 1 to 2, and * and *' may each represent a binding site that is linked to any one of $R_1$ and $R_5$ or any one of a nitrogen atom and a carbon atom of the back bone.

In the structure of Formula 1, one or more of the divalent linkers $L_1$ and $L_2$ may not be present, or $L_1$ and $L_2$ all may not be present. If $L_1$ and $L_2$ all are not present, a and b in Formula 1 are 0. For example, a and b in Formula 1 may each independently be 0 or 1.

The heterocyclic compound represented by Formula 1 may have a high glass transition temperature or melting point due to the introduction of a heterocycle therein. Accordingly, an organic light-emitting diode including the heterocyclic compound represented by Formula 1 may exhibit a resistance against a Joule's heat generated in an organic layer during light emission, a Joule's heat that is generated between organic layers, or a Joule's heat that is generated between an organic layer and a metallic electrode, and thus has stronger resistance under high-temperature environments. Also, due to the inclusion of an indole structure in the heterocyclic compound represented by Formula 1, a formed organic light-emitting diode may have high durability during preservation and driving. Also, when $R_1$ to $R_8$ include, for example, fluorene groups, an organic light-emitting diode including the heterocyclic compound represented by Formula 1 may have an improved molecular film state. Accordingly, when the heterocyclic compound represented by Formula 1 is used in an organic light-emitting diode, it may be used with excellent luminescence characteristics and a charge transporting capability as an electron injection material or an electron transporting material, which are suitable for full colors, for example, red, green, blue, and white fluorescent and phosphorescent devices. In particular, the heterocyclic compound represented by Formula 1 may be suitable for use as a light-emitting material of green, blue, white fluorescent devices.

Nonlimiting examples of the heterocyclic compound represented by Formula 1 may include compounds represented by Compounds 1 to 61, below:

1

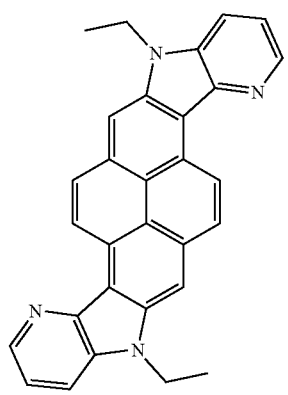

2
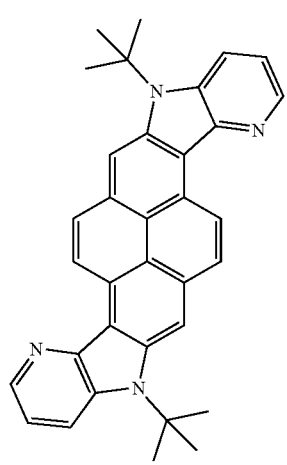
3
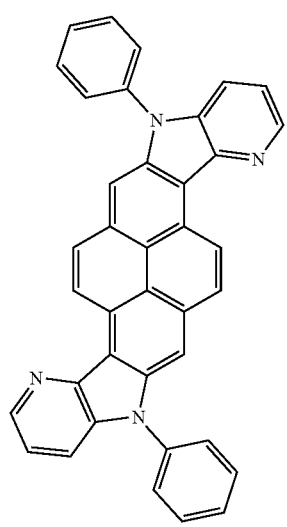
4
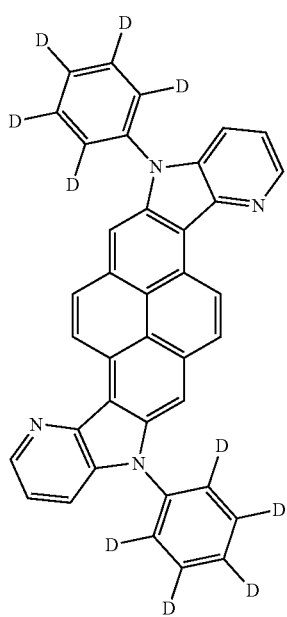
5
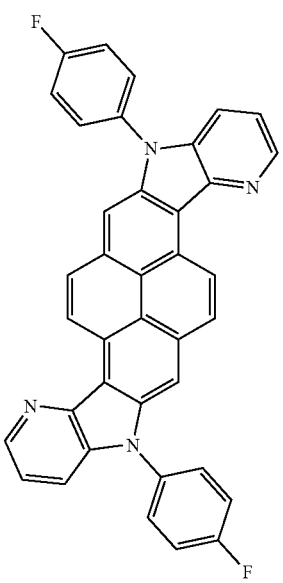
6
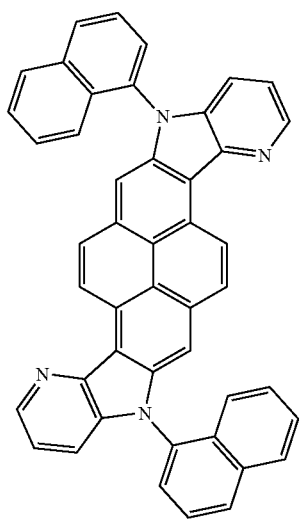

7
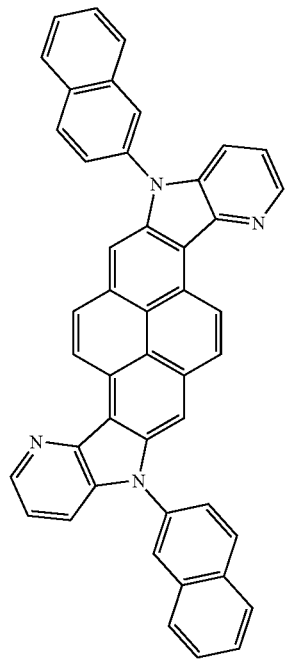
8
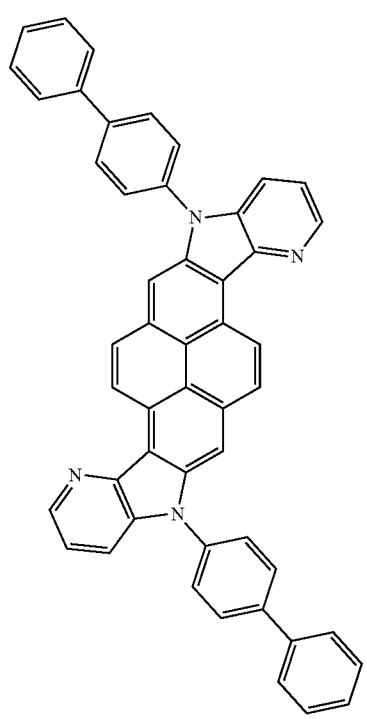
9
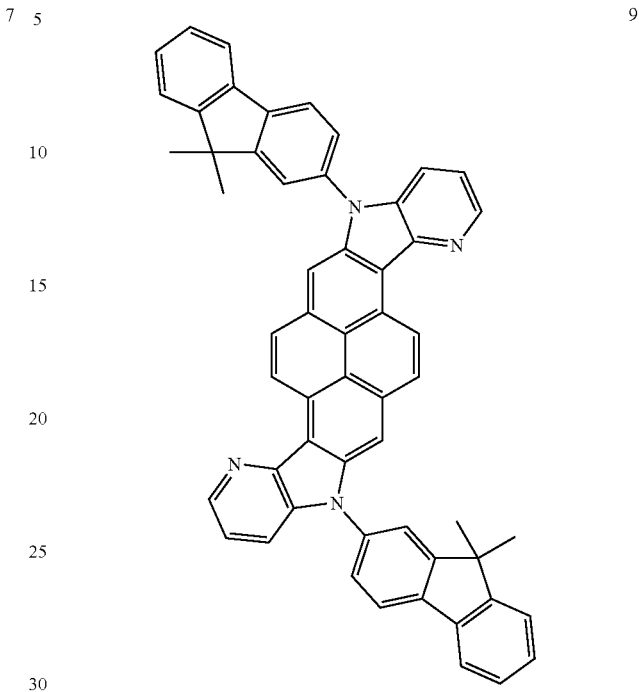
10
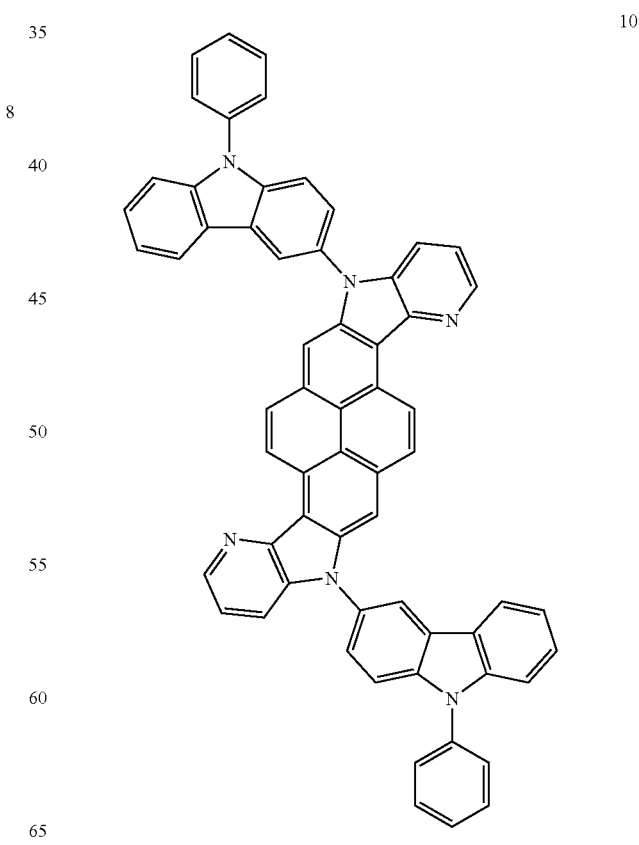

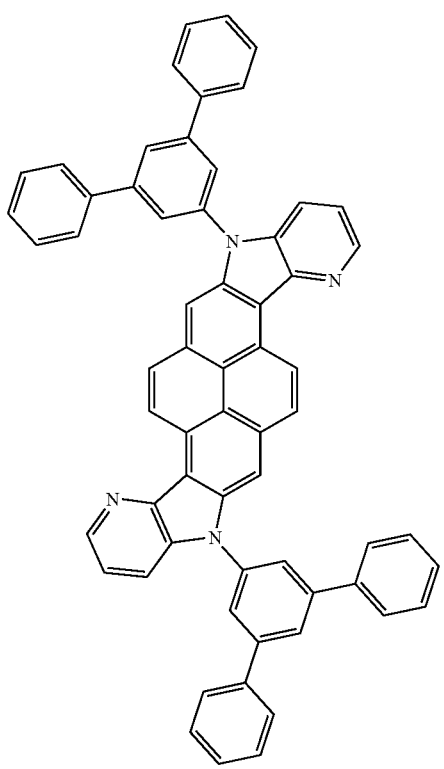
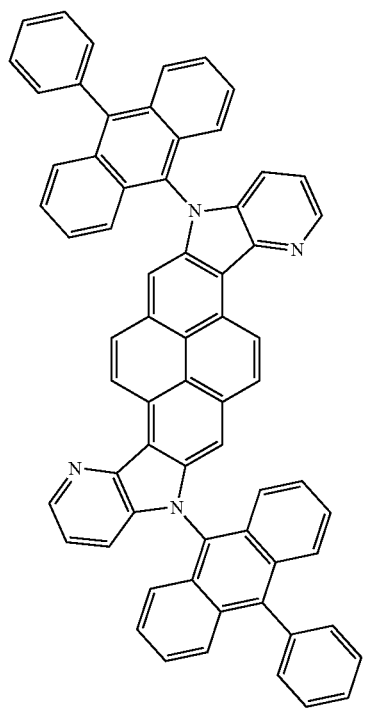
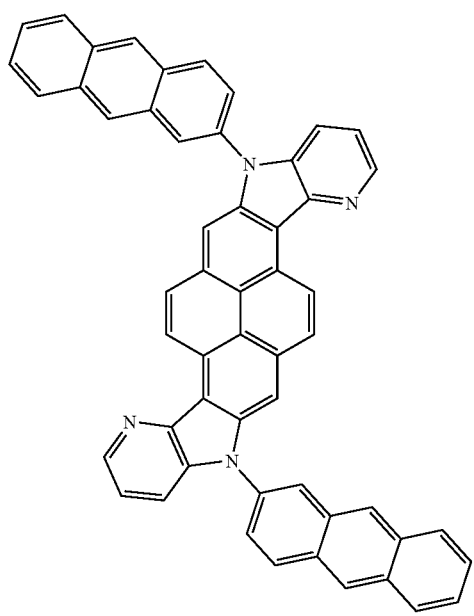
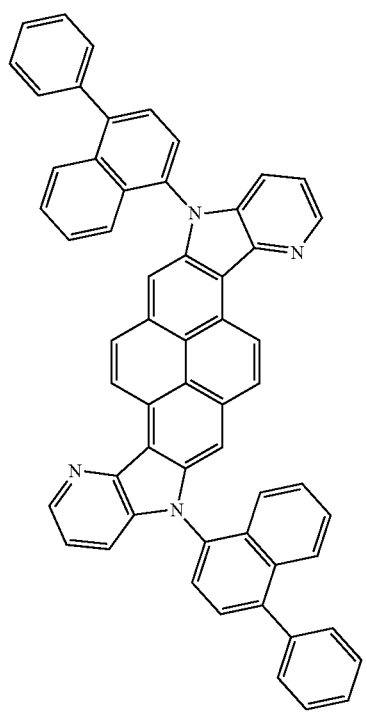

14
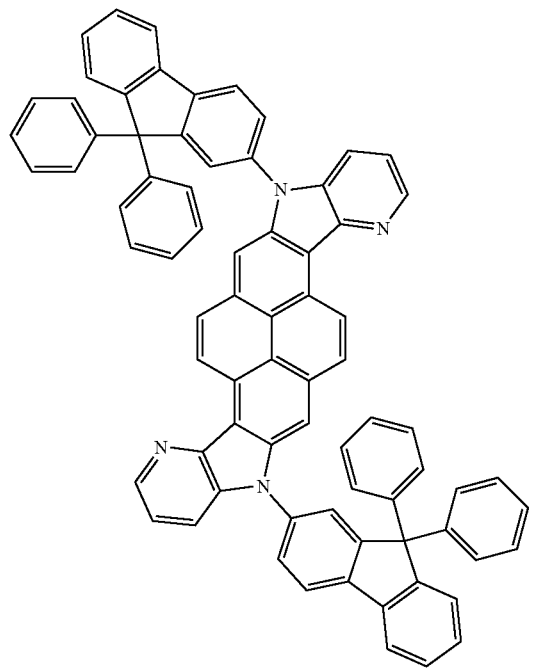
15
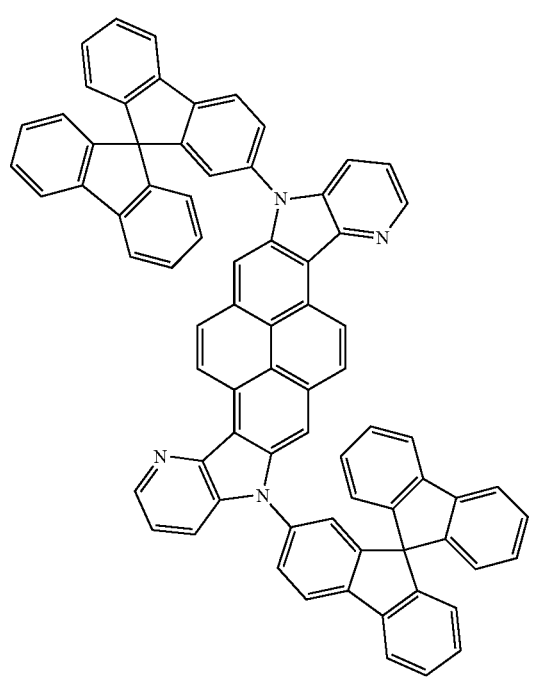
16
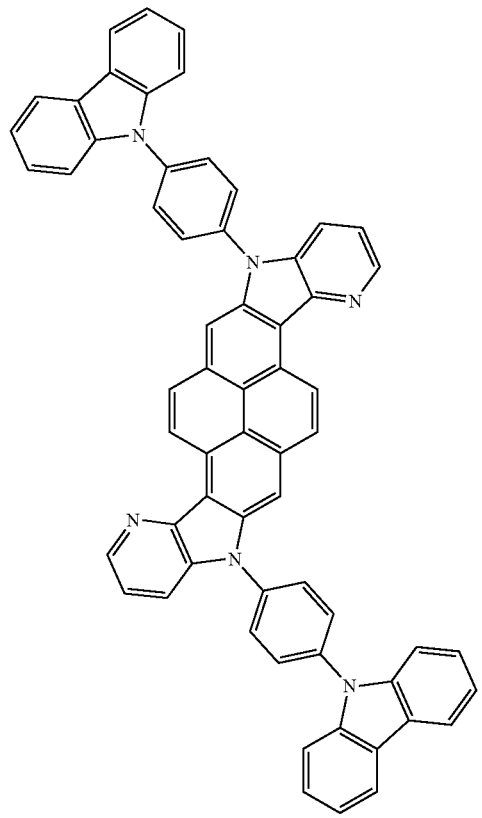
17
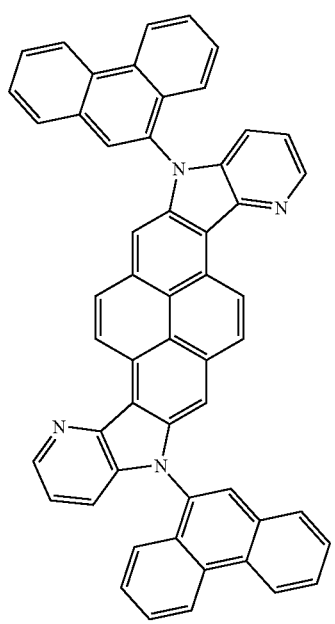

18
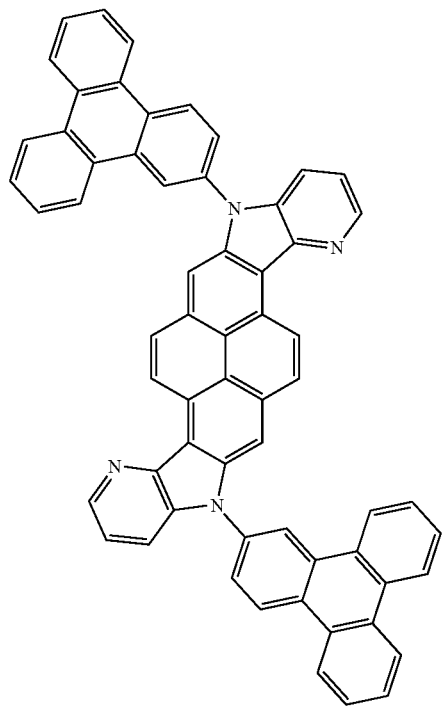
19
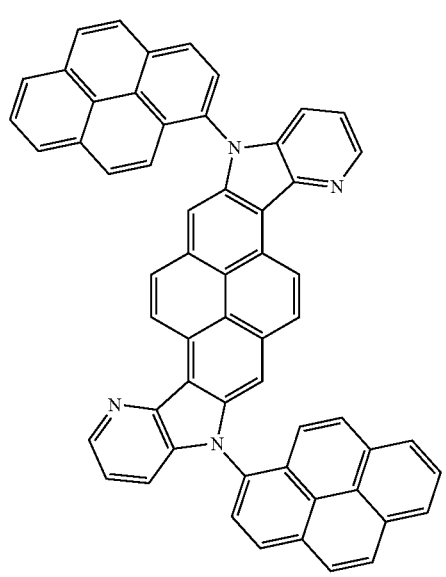
20
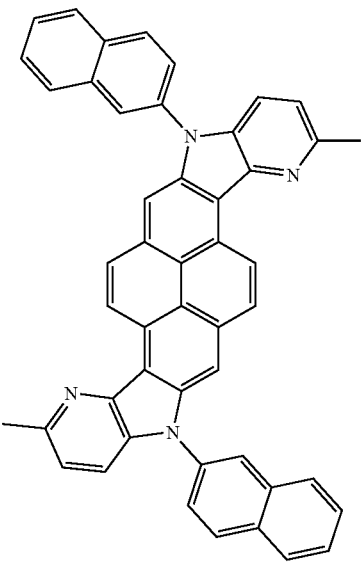
21
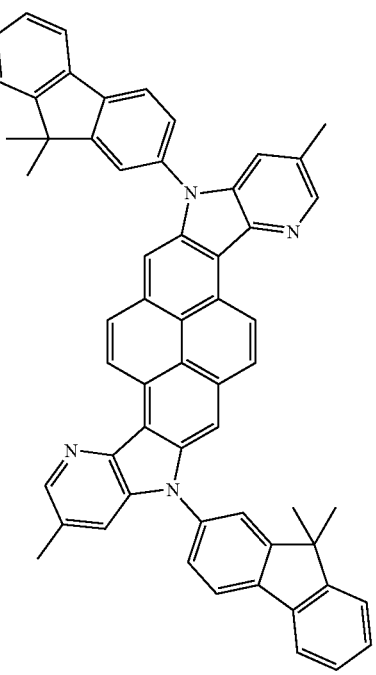

22
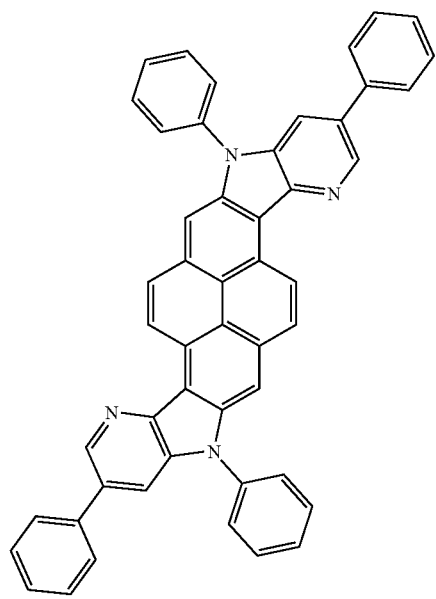
23
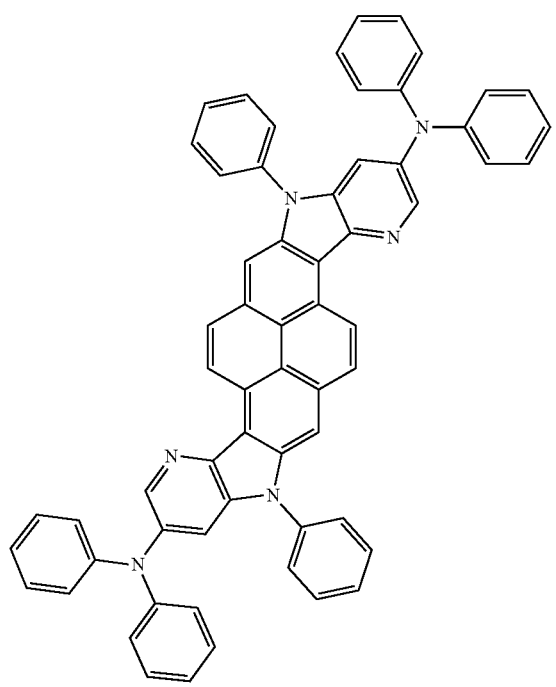
24
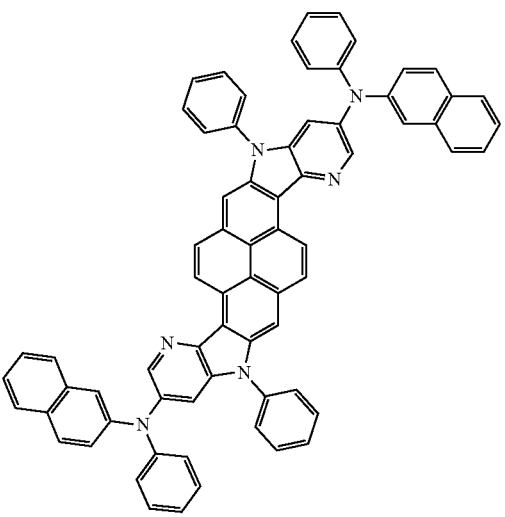
25
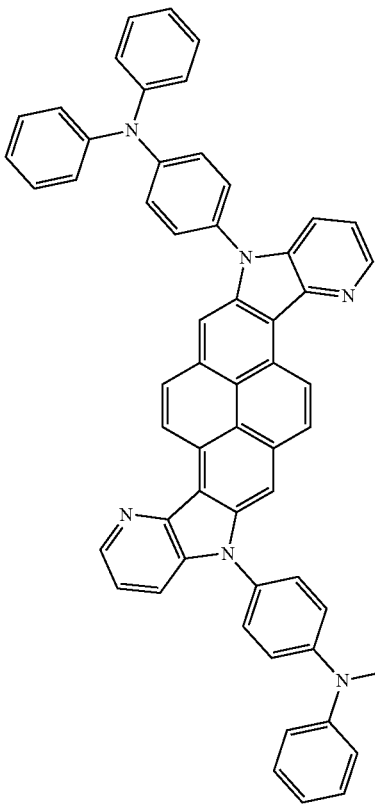

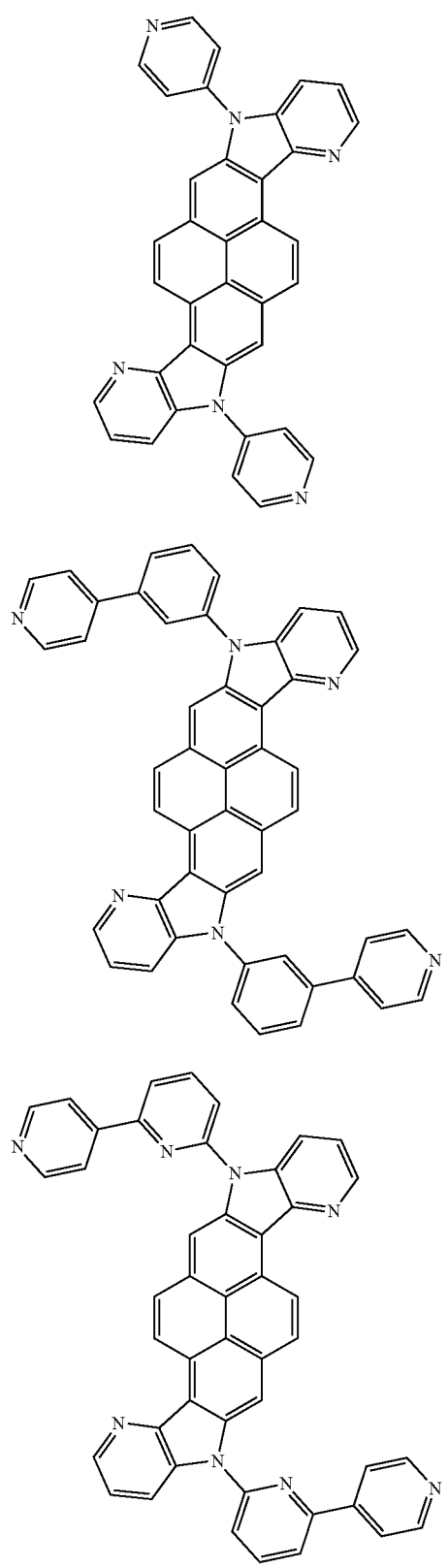
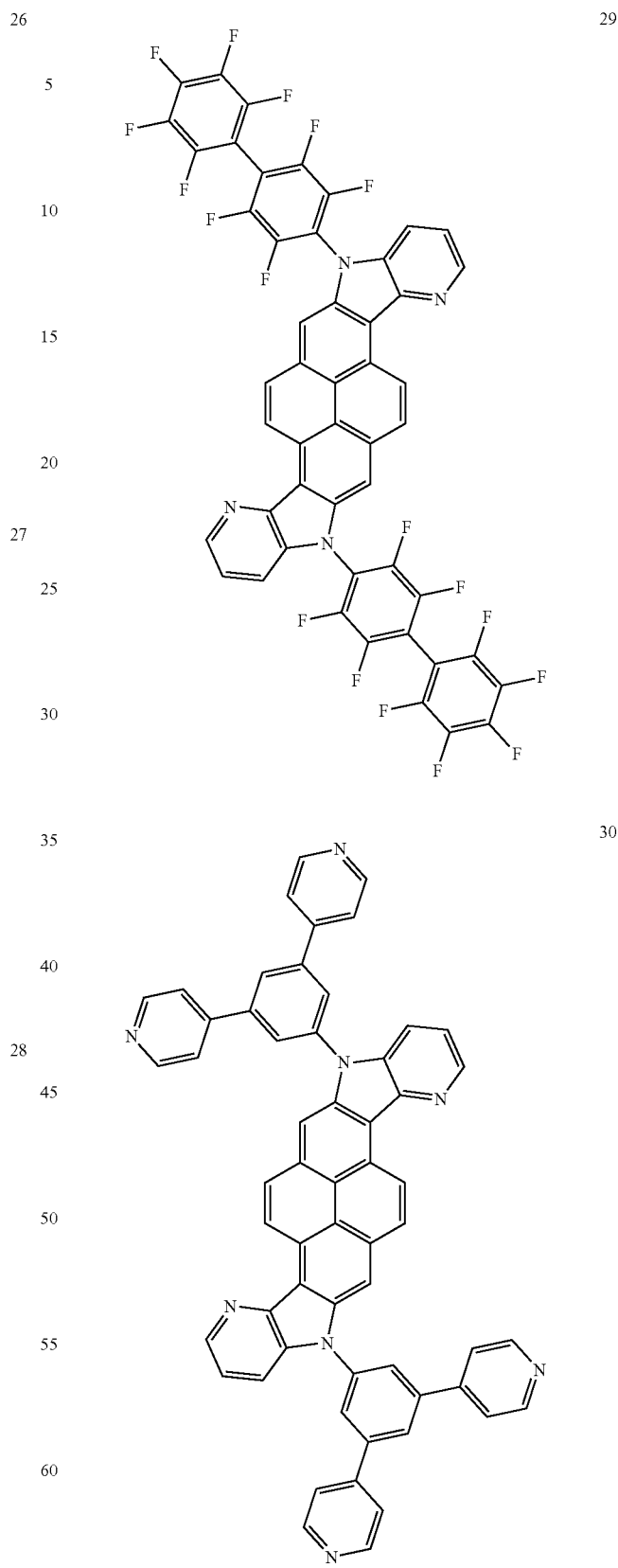

31
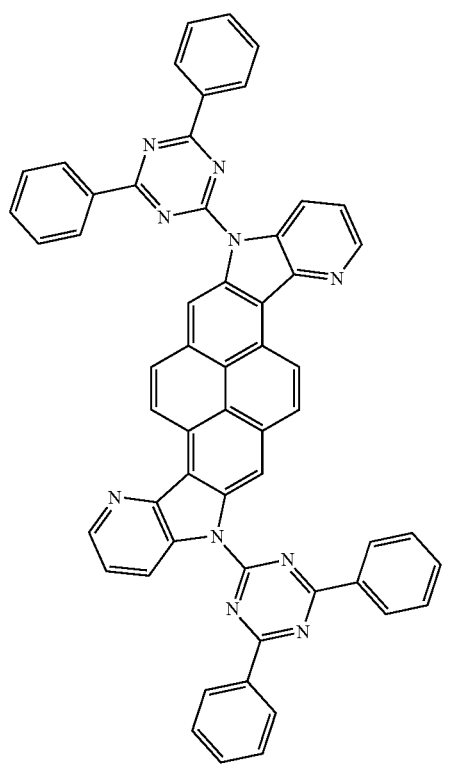
32
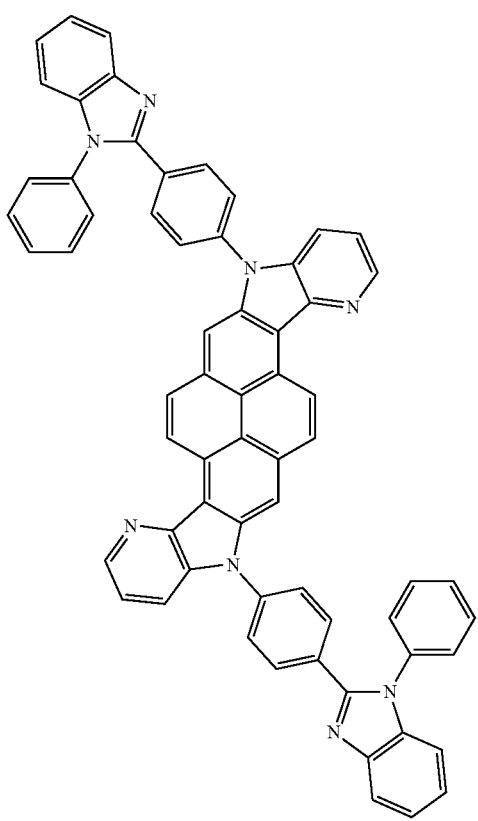
33
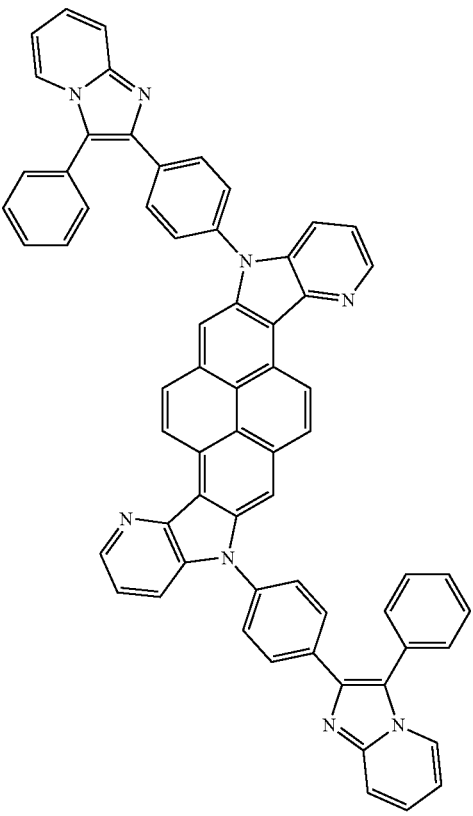
34
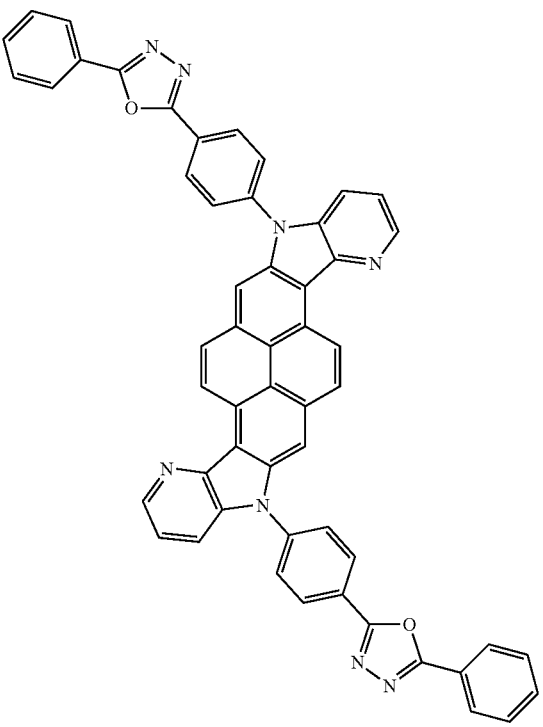

35
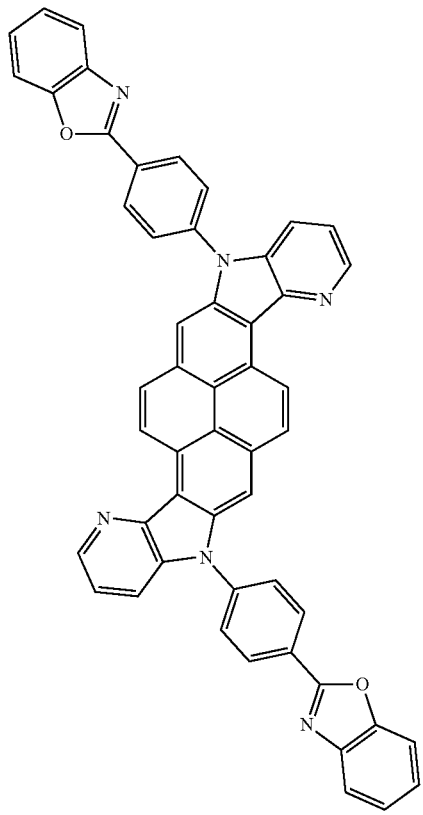
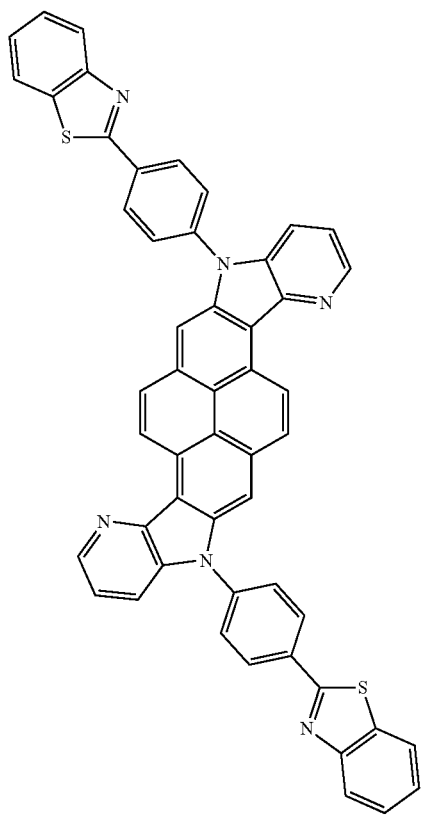
36
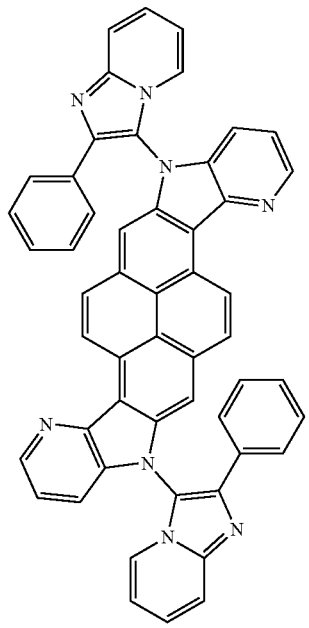
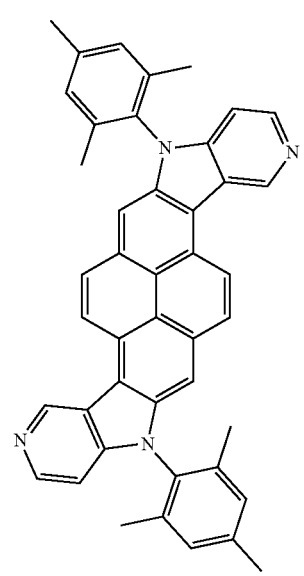

37
-continued
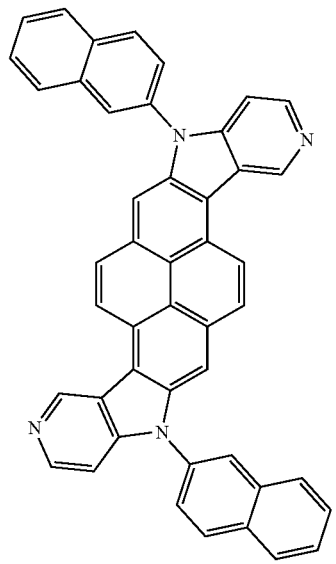
39
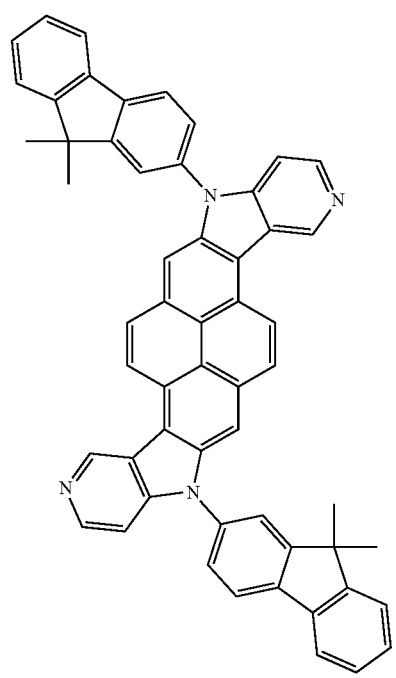
40
38
-continued
41
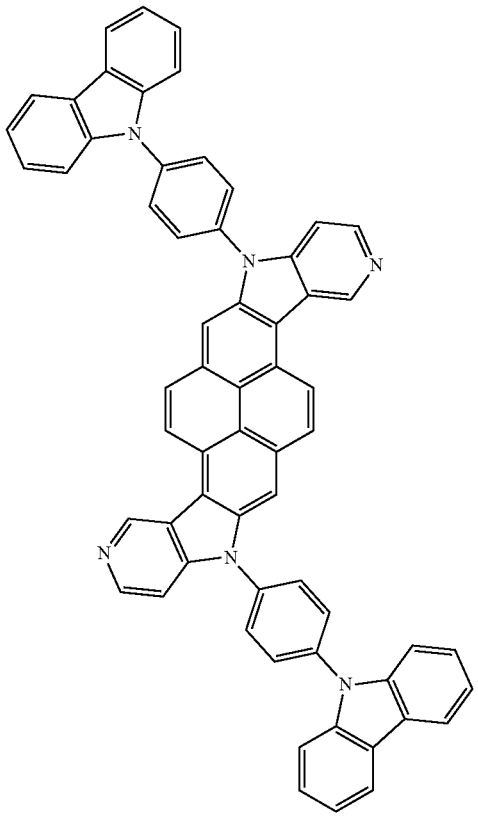
42
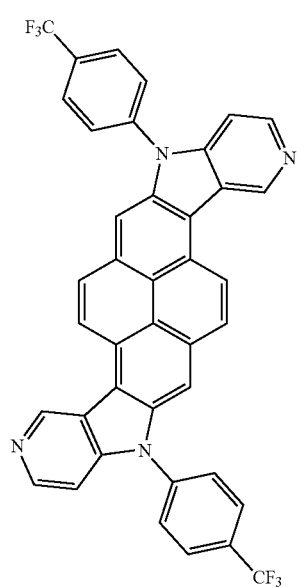

43
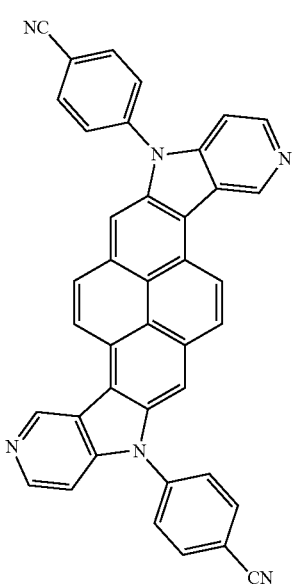
44
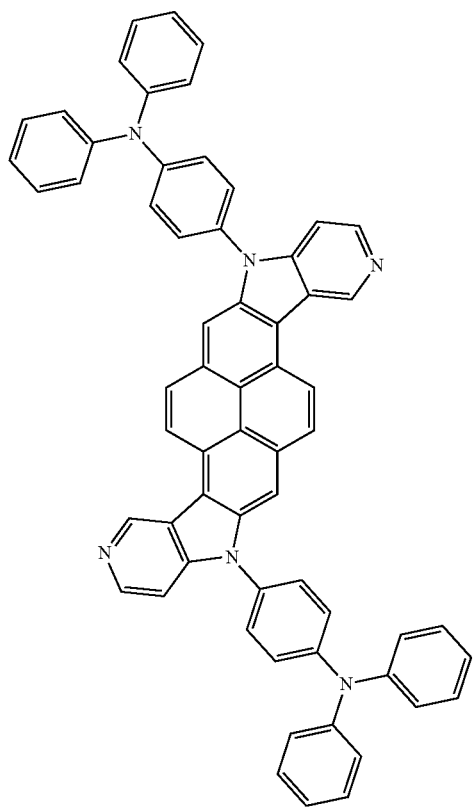
45
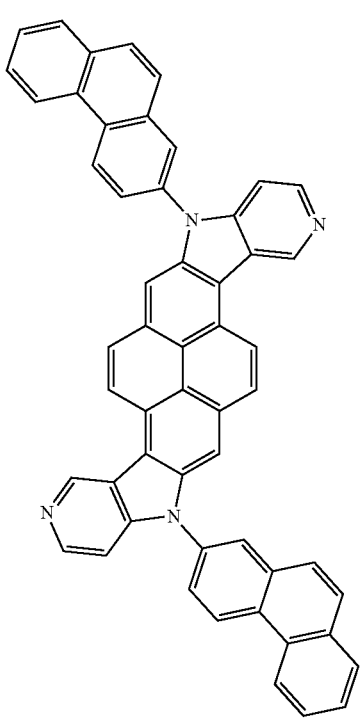
46
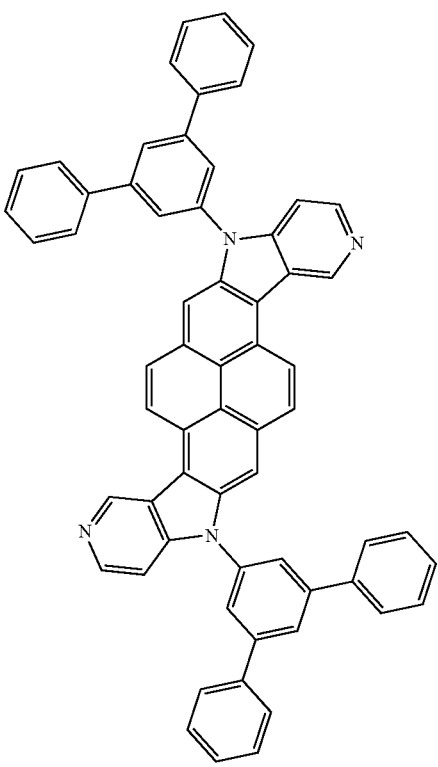

47
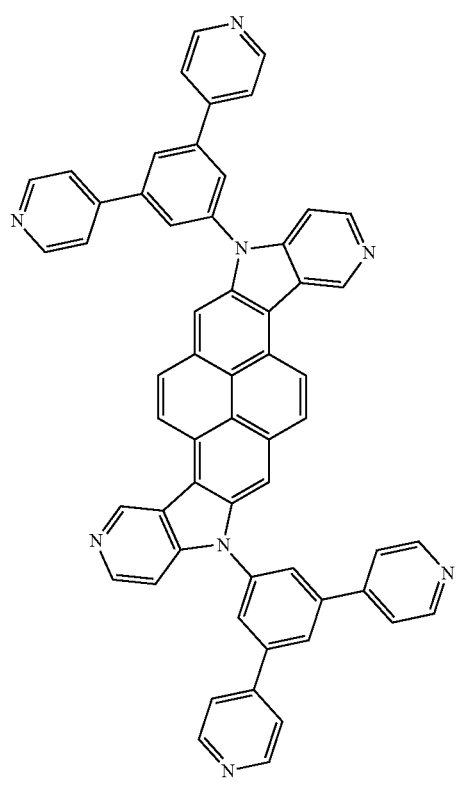
48
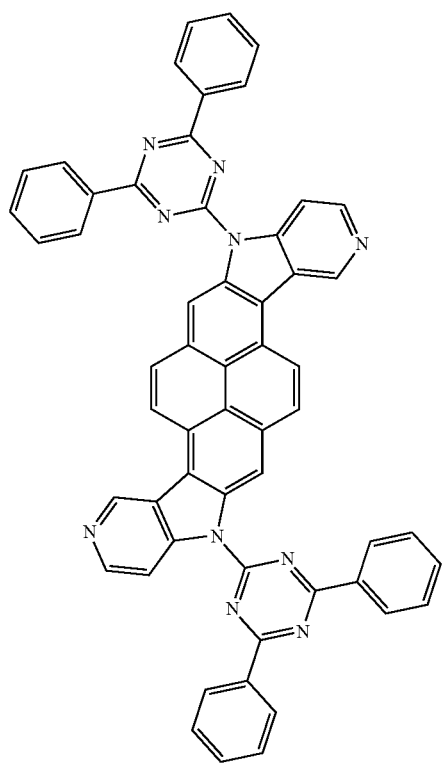
49
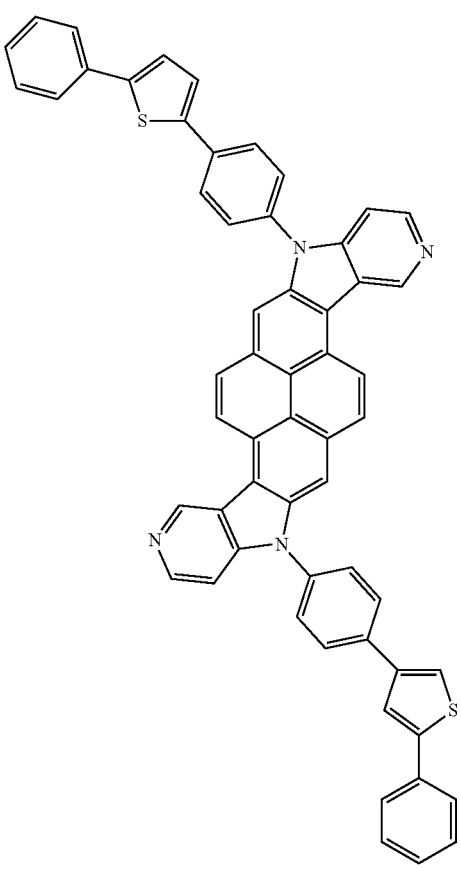
50
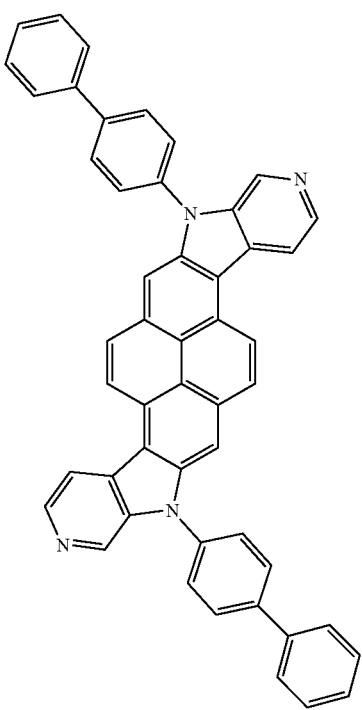

51
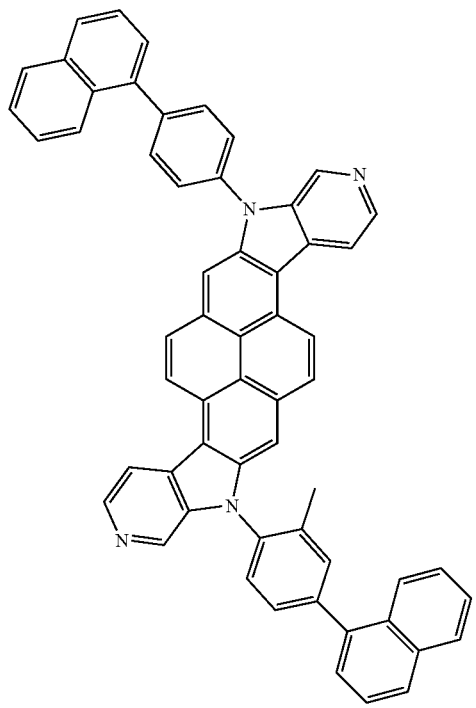
52
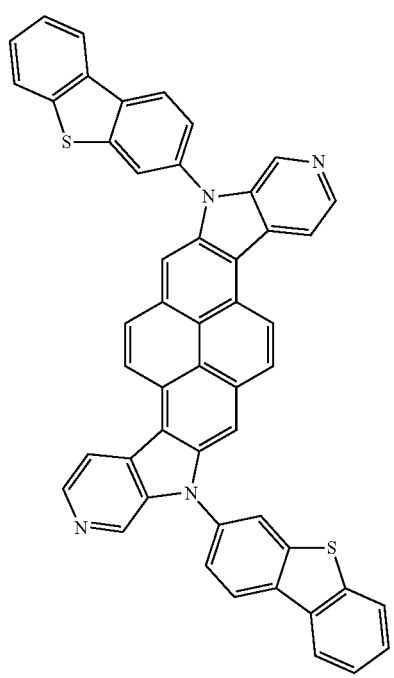
53
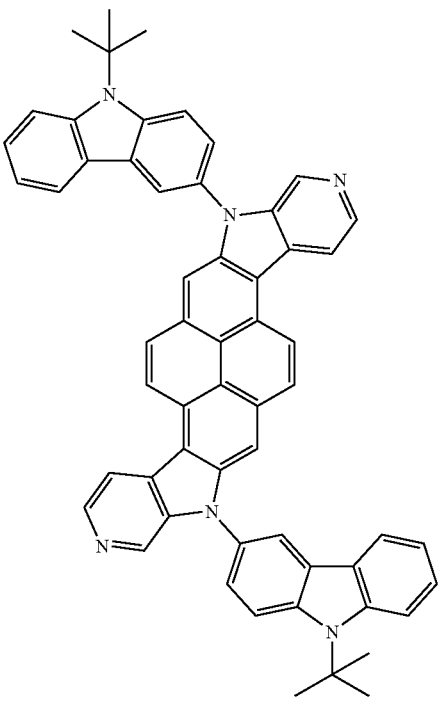
54
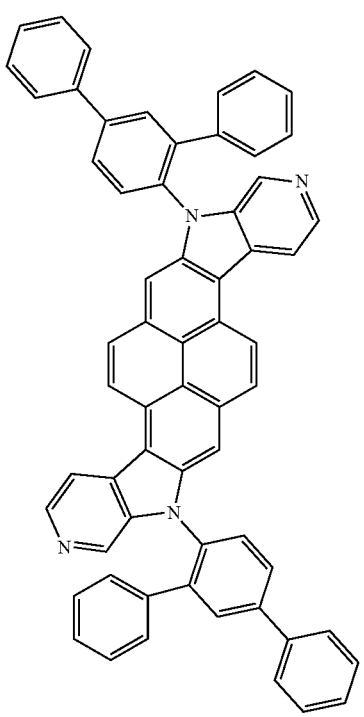

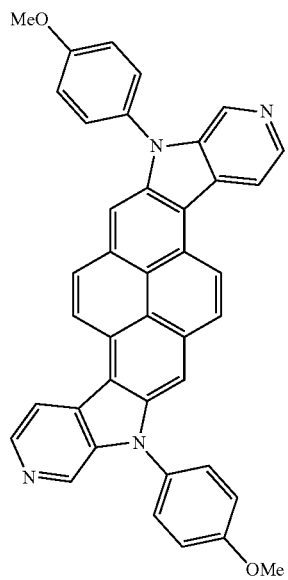
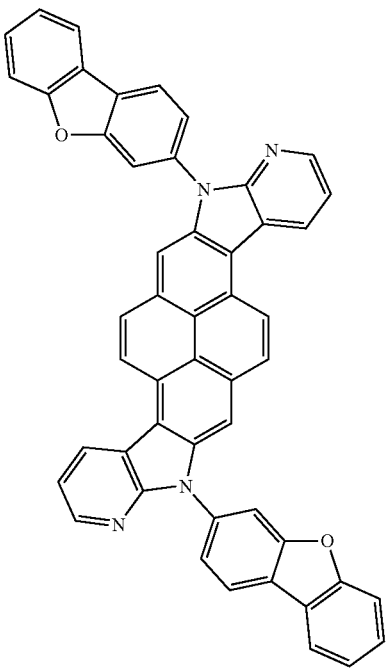
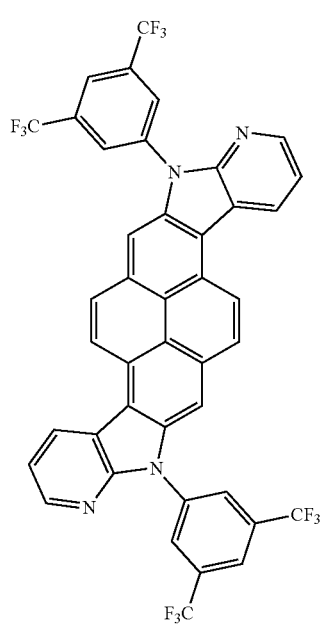
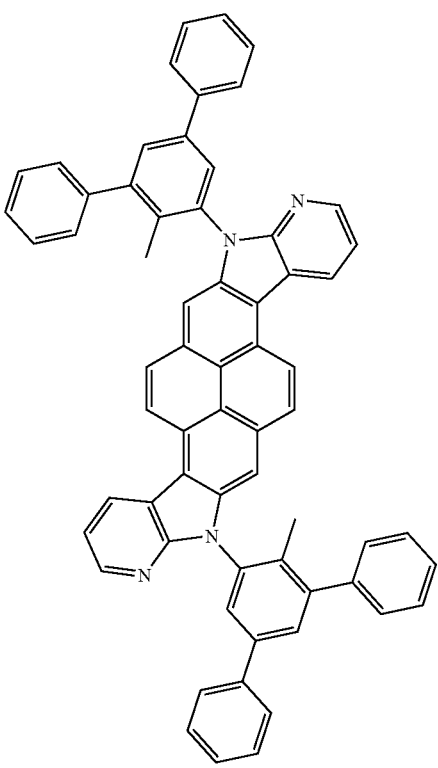

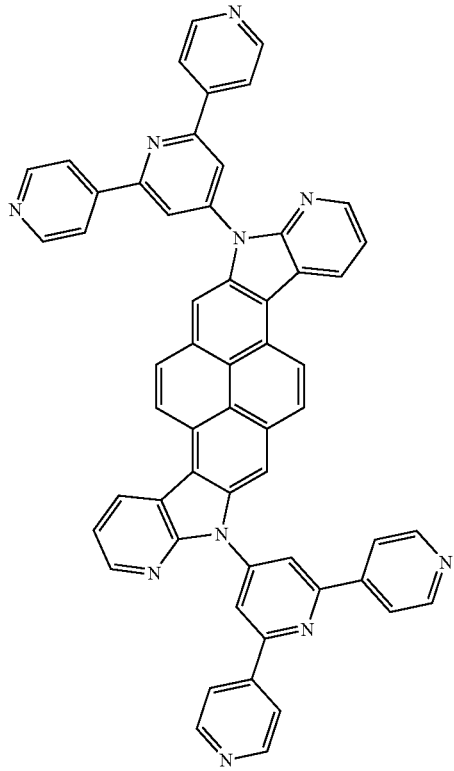

59

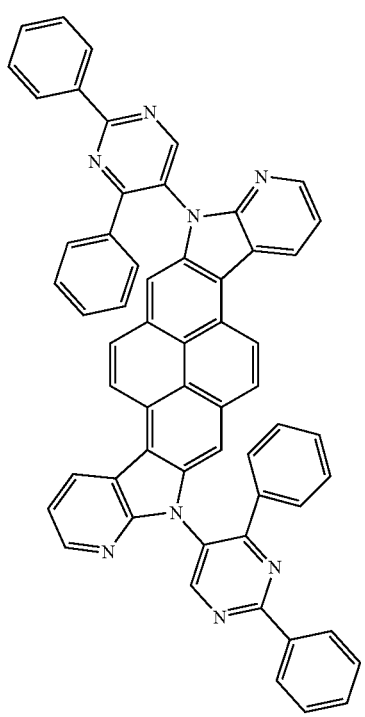

60

61

The term "substituted X" in the term "substituted or unsubstituted A (where A is an arbitrary substituent)" used herein may refer to "a case in which one or more hydrogen atoms of the A are substituted with a deuterium atom, a halogen atom, a hydroxyl group, a cyano group, a nitro group, a carboxyl group or a salt derivative thereof, a sulfonic acid group or a salt derivative thereof, a phosphoric acid group or a salt derivative thereof, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{30}$ cyclo alkyl group, a $C_3$-$C_{30}$ cyclo alkenyl group, a $C_6$-$C_{30}$ aryl group, a $C_6$-$C_{30}$ aryloxy group, a $C_6$-$C_{30}$ arylthio group, a $C_3$-$C_{30}$ hetero aryl group, a group represented by N($Q_{101}$)($Q_{102}$), or a group represented by Si($Q_{103}$)($Q_{104}$)($Q_{105}$) wherein $Q_{101}$ to $Q_{105}$ are each independently a hydrogen atom, a deuterium atom, a halogen atom, a hydroxyl group, a cyano group, an amino group, a nitro group, a carboxyl group, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{30}$ cyclo alkyl group, a $C_3$-$C_{30}$ cyclo alkenyl group, a $C_6$-$C_{30}$ aryl group, a $C_6$-$C_{30}$ aryloxy group, a $C_6$-$C_{30}$ arylthio group, or a $C_3$-$C_{30}$ hetero aryl group.

For example, the term "substituted A" may refer to "a case in which one or more hydrogen atoms of the A are substituted with a deuterium atom, a halogen atom, a hydroxyl group, a cyano group, a nitro group, a carboxyl group, a methyl group, an ethyl group, a propyl group, a butyl group, a pentyl group, a phenyl group, a non-phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, a phenanthridinyl group, a phenanthrollinyl group, an anthryl group, a fluorantenyl group, a triphenylenyl group, a pyrenyl group, a chricenyl group, a naphthacenyl group, a pycenyl group, a perylenyl group, a pentaphenyl group, a hexacenyl group, a pyrrolyl group, an imidazolyl group, a benzoimidazolyl group, a pyrazolyl group, a pyridinyl group, an imidazopyridinyl group, a pyrazinyl group, a pyrimidinyl group, an imidazopyrimidinyl group, a pyridazinyl group, an indolyl group, an isoindolyl group, a pyrido indolyl group, an indazolyl group, a purinyl group, a quinolinyl group, a benzoquinolinyl group, a phthallazinyl group, a naphthyridinyl group, a quinoxalinyl group, a quinazolinyl group, a carbazolyl group, a phenazinyl group, a puranyl group, a benzopuranyl group, a dibenzopuranyl group, a thiophenyl group, a benzothiophenyl group, a dibenzothiophenyl group, a thiazolyl group, an isothiazolyl group, a benzothiazolyl group, an oxazolyl group, a benzooxazolyl group, an isooxazolyl group, an oxadiazolyl group, a triazolyl group, a triazinyl group, a tetrazolyl group, a group represented by $N(Q_{101})(Q_{102})$, or a group represented by $Si(Q_{103})(Q_{104})(Q_{105})$.

The unsubstituted $C_1$-$C_{30}$ alkyl group may refer to a linear or branched saturated hydrocarbonyl group of alkane from which one hydrogen atom is deficient. Examples of the unsubstituted $C_1$-$C_{30}$ alkyl group are methyl, ethyl, propyl, isobutyl, sec-butyl, pentyl, iso-amyl, hexyl, etc. A substituent of the substituted $C_1$-$C_{30}$ alkyl group may be any one of the substituents presented above where the term "substituted A" is described in detail.

The unsubstituted $C_2$-$C_{30}$ alkenyl group used herein may refer to a terminal group having at least one carbon-carbon double blond at the center or at a terminal of the substituted and unsubstituted $C_2$-$C_{30}$ alkyl group. Nonlimiting examples of the unsubstituted $C_2$-$C_{30}$ alkenyl group are an ethenyl group, a propenyl group, a butenyl group, a pentenyl group, a hexenyl group, a heptenyl group, an octenyl group, a propadienyl group, an isoprenyl group, and an allyl group. A substituent of the substituted $C_2$-$C_{30}$ alkenyl group may be any one of the substituents presented above where the term "substituted A" is described in detail.

The unsubstituted $C_2$-$C_{30}$ alkynyl group used herein may refer to a terminal group having at least one carbon-carbon triple bond at the center or at a terminal of the substituted and unsubstituted $C_2$-$C_{30}$ alkyl group. Nonlimiting examples of the unsubstituted $C_2$-$C_{30}$ alkynyl group are acetylenyl group, etc. A substituent of the substituted $C_2$-$C_{30}$ alkynyl group may be any one of the substituents presented above where the term "substituted A" is described in detail.

The unsubstituted $C_1$-$C_{30}$ alkoxy group used herein may have a formula represented by —OY where Y is the unsubstituted $C_1$-$C_{30}$ alkyl group as defined above. Nonlimiting examples of the unsubstituted $C_1$-$C_{30}$ alkoxy group are methoxy, ethoxy, isopropyloxy, butoxy, pentoxy, etc. A substituent of the substituted $C_1$-$C_{30}$ alkoxy group may be any one of the substituents presented above where the term "substituted A" is described in detail.

The unsubstituted $C_3$-$C_{30}$ cycloalkyl group used herein may refer to a cyclic saturated hydrocarbonyl group. Nonlimiting examples of the unsubstituted $C_3$-$C_{30}$ cycloalkyl group are cyclopropyl group, cyclobutyl group, cyclopentyl group, cyclohexyl group, cyclooctyl group, etc. A substituent of the substituted $C_1$-$C_{30}$ cycloalkyl group may be any one of the substituents presented above where the term "substituted A" is described in detail.

The unsubstituted $C_3$-$C_{30}$ cycloalkenyl group used herein may refer to a cyclic unsaturated hydrocarbonyl group having one or more carbon double bonds that are not an aromatic ring. Nonlimiting examples of the unsubstituted $C_3$-$C_{30}$ cycloalkenyl group are a cyclopropenyl group, a cyclobutenyl group, a cyclopentenyl group, a cyclohexenyl group, a cyclo-heptenyl group, a 1,3-cyclohexadienyl group, a 1,4-cyclohexadienyl group, a 2,4-cycloheptadienyl group, a 1,5-cyclooctadienyl group, etc. A substituent of the substituted $C_3$-$C_{30}$ cycloalkenyl group may be any one of the substituents presented above where the term "substituted A" is described in detail.

The unsubstituted $C_6$-$C_{30}$ aryl group used herein may refer to a monovalent group having a carbocyclic aromatic system in which the number of carbon atoms is 6 to 30, and may be a monocyclic group or a polycyclic group. If the unsubstituted $C_6$-$C_{30}$ aryl group is a polycyclic group, two or more rings contained in the unsubstituted $C_6$-$C_{30}$ aryl group may be fused. Nonlimiting examples of the unsubstituted $C_6$-$C_{30}$ aryl group are a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthryl group, a fluoranthenyl group, a triphenylenyl group, a pyrenyl group, a chrysenyl group, a naphthacenyl group. a picenyl group, a perylenyl group, a pentaphenyl, and a hexacenyl. A substituent of the substituted $C_6$-$C_{30}$ aryl group may be any one of the substituents presented above where the term "substituted A" is described in detail.

The unsubstituted $C_6$-$C_{30}$ aryloxy group used herein may refer to a monovalent group wherein a carbon atom of the $C_6$-$C_{30}$ aryl group is attached via an oxygen linker (—O—). A substituent of the substituted $C_6$-$C_{30}$ aryloxy group may be any one of the substituents presented above where the term "substituted A" is described in detail.

The unsubstituted $C_6$-$C_{30}$ arylthio group used herein may refer to a monovalent group wherein a carbon atom of the $C_6$-$C_{30}$ aryl group is attached via a sulfur linker (—S—). Examples of the unsubstituted $C_6$-$C_{30}$ arylthio group are a phenyl thio group, a naphthyl thio group, an indanylthio group, and an indenyl thio group. A substituent of the substituted $C_6$-$C_{30}$ arylthio group may be any one of the substituents presented above where the term "substituted A" is described in detail.

The unsubstituted $C_3$-$C_{30}$ hetero aryl group used herein may refer to a monovalent group that has at least one ring having one or more hetero atoms selected from the group consisting of nitrogen (N), oxygen (O), phosphorous (P), and sulfur (S) and that has 3 to 30 carbon atoms, and may be a monocyclic or polycyclic group. If the unsubstituted $C_3$-$C_{30}$ hetero aryl group is a polycyclic group, two or more rings contained in the unsubstituted $C_3$-$C_{30}$ hetero aryl group may be fused. Examples of the unsubstituted $C_3$-$C_{30}$ hetero aryl group are a pyrrolyl group, an imidazolyl group, a pyrazolyl group, a pyridinyl group, a pyrazinyl group, a pyrimidinyl group, a pyridazinyl group, an isoindolyl group, an indolyl group, anindazolyl group, a purinyl group, a quinolinyl group, a benzoquinolinyl group, a phthalazinyl group, anaphthyridinyl group, a quinoxalinyl group, a quinazolinyl group, a cinnolinyl group, a carbazolyl group, phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, thiazolyl group, an isothiazolyl group, a benzothiazolyl group, an isoxazolyl group, an oxazolyl group, a triazolyl group, a tetrazolyl group, an oxadiazolyl group, a triazinyl group, a benzooxazolyl group, etc. A substituent of the substituted $C_3$-$C_{30}$ hetero aryl group may be any one of the substituents presented above where the term "substituted A" is described in detail.

The unsubstituted $C_1$-$C_{30}$ alkylene group used herein may be a linear or branched divalent group of alkane from which two hydrogen atoms are deficient. Examples of the unsubstituted $C_1$-$C_{30}$ alkylene group may be understood by referring to the examples of the unsubstituted $C_1$-$C_{30}$ alkyl group presented above. A substituent of the substituted $C_1$-$C_{30}$ may be any one of the substituents presented above where the term "substituted A" is described in detail.

The unsubstituted $C_6$-$C_{30}$ arylene used herein may refer to a divalent group having a carbocyclic aromatic system having 6 to 30 carbon atoms, and the divalent group may be a monocyclic or polycyclic group. Examples of the unsubstituted $C_6$-$C_{30}$ arylene may be understood by referring to the examples of the unsubstituted $C_6$-$C_{30}$ aryl group. A substituent of the substituted $C_6$-$C_{30}$ arylene may be any one of the substituents presented above where the term "substituted A" is described in detail.

The unsubstituted $C_3$-$C_{30}$ heteroarylene group used herein may refer to a divalent group that has at least one ring having one or more hetero atoms selected from the group consisting of nitrogen (N), oxygen (O), phosphorous (P), and sulfur (S) and that has 3 to 30 carbon atoms, and may be a monocyclic or polycyclic group. If the unsubstituted $C_3$-$C_{30}$ hetero aryl group is a polycyclic group, two or more rings contained in the unsubstituted $C_3$-$C_{30}$ hetero aryl group may be fused. Examples of the unsubstituted $C_3$-$C_{30}$ heteroarylene group may be understood by referring to the examples of the unsubstituted $C_3$-$C_{30}$ hetero aryl group. A substituent of the substituted $C_3$-$C_{30}$ heteroarylene group may be any one of the substituents presented above where the term "substituted A" is described in detail.

The heterocyclic compound represented by Formula 1 may be synthesized by using known organic synthesis methods. One of the heterocyclic compound synthesis methods will be described in detail, below.

The heterocyclic compound represented by Formula 1 may be used in an organic light-emitting diode.

An embodiment of the present invention provides an organic light-emitting diode including a first electrode, a second electrode facing the first electrode, and at least a first layer interposed between the first electrode and the second electrode, wherein the first layer includes the heterocyclic compound represented by Formula 1, wherein the heterocyclic compound represented by Formula 1 may be used alone, or may be used in a mixed form with other materials.

The first layer may include at least one layer selected from the group of a hole injection layer, a hole transport layer, a functional layer having a hole injection function and a hole transportation function, an electron blocking layer, an emission layer, a hole blocking layer, an electron transport layer, an electron injection layer, and a functional layer having an electron transportation function and an electron injection function.

For example, the organic light-emitting diode may have a structure of first electrode/hole injection layer/hole transport layer/first layer including the heterocyclic compound represented by Formula 1 (e.g., functions as an emission layer)/electron transport layer/electron injection layer/second electrode, but the structure thereof is not limited thereto.

Layers interposed between the first electrode and the second electrode may include, e.g., at least one layer selected from the group of a hole injection layer, a hole transport layer, an emission layer, a hole blocking layer, an electron transport layer, and an electron injection layer, and at least one of these layers may be formed by using a deposition process or a wet process.

The term "wet process" used herein may refer to a process in which a material is mixed with a solvent to prepare a mixture, and the mixture is provided on a substrate, followed by drying and/or heat treating so as to remove at least a portion of the solvent, thereby forming a film including the material on the substrate.

For example, the first layer may be formed by using a typical vacuum deposition method. Alternatively, a mixture including the heterocyclic compound and a solvent may be provided on a first layer formation region (e.g., on an upper portion of a hole transport layer) by spin coating, spraying, ink-jet printing, dipping, casting, Gravia coating, bar coating, roll coating, wire bar coating, screen coating, flexo coating, offset coating, or laser transferring, and then, the mixture provided on the first layer formation region is dried and/or heat treated to remove at least a portion of the solvent, thereby forming the first layer.

Alternatively, after a first layer is formed on a base film by using the wet process as described above, the first layer may be transferred to a first layer formation region (for example, an upper portion of the hole transport layer) by using, for example, a laser.

The first layer may be an emission layer. When the first layer is an emission layer, the emission layer may include at least one selected from the group consisting of a fluorescent host, a phosphorescent host, a fluorescent dopant, and a phosphorescent dopant.

For example, the first layer may be an emission layer, and the heterocyclic compound of Formula 1 included in the first layer may be used as a fluorescent host or a phosphorescent host. In this regard, the first layer may further include a fluorescent dopant or a phosphorescent dopant. For example, the first layer may be either an emission layer that includes the heterocyclic compound of Formula 1 functioning as a fluorescent host, and a fluorescent dopant, or an emission layer that includes the heterocyclic compound of Formula 1 functioning as a phosphorescent host, and a phosphorescent dopant. Also, the emission layer may include the heterocyclic compound, wherein i) the heterocyclic compound functions as a fluorescent host, ii) the heterocyclic compound functions as a fluorescent dopant, or iii) the heterocyclic compound functions as both a fluorescent host and a fluorescent dopant.

According to an embodiment, the first layer may be an emission layer, wherein the emission layer includes at least one selected from the group of an anthracene-based compound, an arylamine-based compound, and a styryl-based compound.

The emission layer may include the heterocyclic compound described above.

According to an embodiment, the first layer may be an electron transport layer, wherein the electron transport layer may include the heterocyclic compound described above.

According to an embodiment, the first layer may include an emission layer and an electron transport layer, and each of the emission layer and the electron transport layer may include the heterocyclic compound described above.

For example, the first layer included in the organic light-emitting diode may be an electron transport layer, an emission layer may be additionally interposed between the first electrode and the second electrode, and the emission layer may include at least one region selected from the group of a red light-emitting region, a green light-emitting region, a blue light-emitting region, and a white light-emitting region, wherein the at least one region selected from the group of the red light-emitting region, green light-emitting region, the blue light-emitting region, and the white light-emitting region includes a phosphorescent compound. The red light-emitting region, the green light-emitting region, the blue light-emitting region, and the white light-emitting region may be patterned by using known methods so as to embody full color images or white light emission. The phosphorescent compound may be selected from known phosphorescent hosts and phosphorescent dopants.

The first layer may include an electron transport layer, which may include a metal-containing compound. The metal-containing compound is the same as described above.

The first layer may include at least one selected from the group of a hole injection layer, a hole transport layer, and a functional layer having a hole injection function and a hole transportation function, wherein the at least one selected from the group of the hole injection layer, the hole transport layer, and the functional layer having a hole injection function and a hole transportation function may further include a charge generation material. The charge generation material may improve conductivity of the first layer.

The charge generation material may be, for example, a p-dopant. Nonlimiting examples of the p-dopant are quinine derivatives, such as tetracyanoquinodimethane (TCNQ) or 2,3,5,6-tetrafluoro-tetracyano-1,4-benzoquinodimethane (F4TCNQ); metallic oxides, such as tungsten oxide or molybdenum oxide; and cyano group-containing compounds, such as Compound 300 illustrated below.

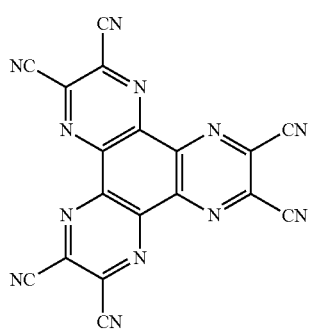
<Compound 300>

If the at least one selected from the group of the hole injection layer, the hole transport layer, and the functional layer having a hole injection function and a hole transportation function further includes the charge generation material, the charge generation material may be homogeneously or non-homogeneously dispersed in the layers. However, the structure of the charge generation material in the layers is not limited thereto.

FIG. 1 illustrates a schematic view of an organic light-emitting diode 10 according to an embodiment. Hereinafter, with reference to FIG. 1, the structure of an organic light-emitting diode according to an embodiment, and a method of manufacturing the organic light-emitting diode, according to an embodiment, will be described in detail.

The organic light-emitting diode 10 may sequentially include a substrate 11, a first electrode 12, a hole injection layer 13, a hole transport layer 14, an emission layer 15, an electron transport layer 16, an electron injection layer 17, and a second electrode 18 in this stated order.

The substrate 11 may be any one of various substrates that are used in a known organic light-emitting device, and may be a glass substrate or a transparent plastic substrate with excellent mechanical strength, thermal stability, transparency, surface smoothness, ease of handling, and water repellency.

The first electrode 12 may be formed by providing a first electrode material on a substrate by deposition or sputtering. If the first electrode 12 is an anode, to allow holes to be injected thereinto easily, the first electrode material may be selected from materials having a high work function. Also, the first electrode 12 may be a reflection electrode or a transmission electrode. The first electrode material may be a transparent and highly conductive material, such as an indium tin oxide (ITO), or an indium zinc oxide (IZO), tin oxide ($SnO_2$), zinc oxide (ZnO), etc. Alternatively, if magnesium (Mg), aluminum (Al), aluminum-lithium (Al—Li), calcium (Ca), magnesium-indium (Mg—In), magnesium-silver (Mg—Ag) etc, are used as the first electrode material, the first electrode 12 may be formed as a reflection electrode. The first electrode 12 may include two different materials. For example, the first electrode 12 may have a two-layer structure including two different materials. However, the structure of the first electrode 12 is not limited thereto.

The hole injection layer 13 may be formed on the first electrode 12.

The hole injection layer 13 may be formed on the first electrode 12 by using various methods, such as vacuum deposition, wet process, laser transferring, etc., as described above.

When the hole injection layer 13 is formed by vacuum deposition, the deposition conditions may vary according to a material that is used to form the hole injection layer 13, and the structure and thermal characteristics of the hole injection layer 13. For example, the deposition conditions may include a deposition temperature of about 100 to about 500° C., a vacuum pressure of about $10^{-8}$ to about $10^{-3}$ torr, and a deposition rate of about 0.01 to about 100 Å/sec. However, the deposition conditions are not limited thereto.

When the hole injection layer 13 is formed using spin coating as a wet process, coating conditions may vary according to the material used to form the hole injection layer 13, and the structure and thermal properties of the hole injection layer 13. For example, a coating speed may be from about 2000 rpm to about 5000 rpm, and a temperature at which a heat treatment is performed to remove a solvent after coating may be from about 80° C. to about 200° C. However, the coating conditions are not limited thereto.

A hole injection layer material may be any one of known hole injecting materials. Non-limiting examples of the hole injection layer material are a phthalocyanine compound, such as copper phthalocyanine, m-MTDATA (a structure thereof is illustrated below), TDATA (a structure thereof is illustrated below), 2-TNATA (a structure thereof is illustrated below), polyaniline/dodecylbenzenesulfonic acid (Pani/DBSA), poly (3,4-ethylenedioxythiophene)/poly(4-styrenesulfonate) (PEDOT/PSS), polyaniline/camphor sulfonic acid (Pani/CSA), polyaniline/poly(4-styrenesulfonate) (Pani/PSS), etc.

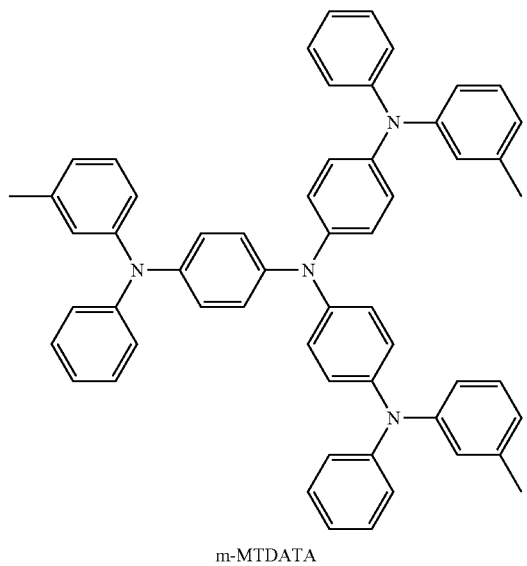
m-MTDATA

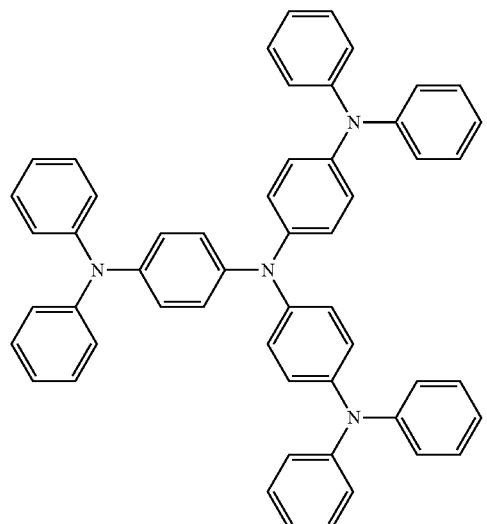

TDATA

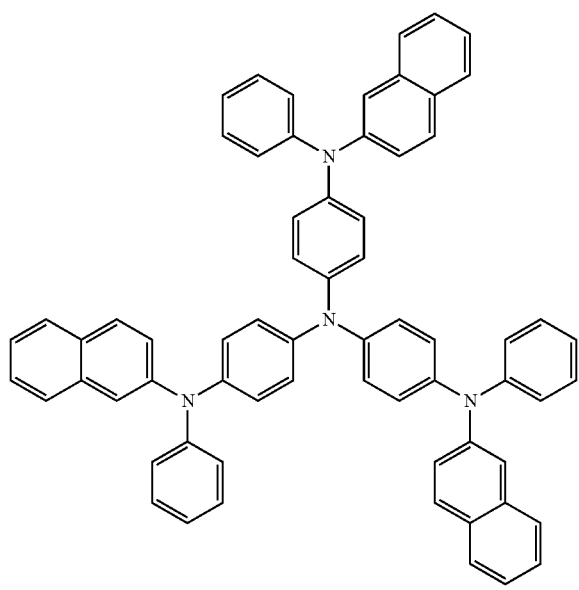

2-TNATA

The hole injection layer 13 may have a thickness of about 100 Å to about 10,000 Å, for example, a thickness of about 100 Å to about 1,000 Å. When the thickness of the hole injection layer 13 is within these ranges, the hole injection layer 13 may have satisfactory hole injection characteristics without an increase in driving voltage.

The hole transport layer 14 may be formed on the hole injection layer 13 by, for example, the vacuum deposition, wet process, or laser transferring.

When the hole transport layer 14 may be formed on the hole injection layer 13 by vacuum deposition or spin coating, the deposition or coating conditions may be similar to those applied to form the hole injection layer 13, although the deposition or coating conditions may vary according to the material that is used to form the hole transport layer 14.

A hole transport layer material may be any one of known hole transport materials. Non-limiting examples of the hole transport layer material are TPD (a structure thereof is illustrated below), NPB (a structure thereof is illustrated below), etc.

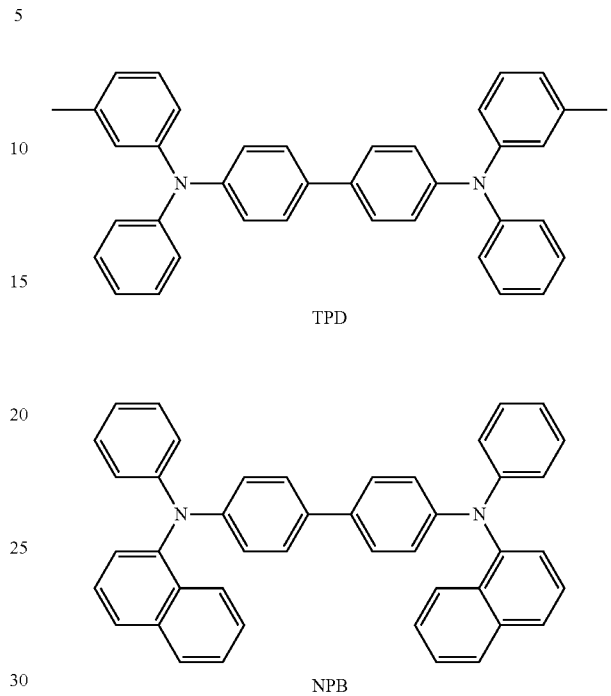

TPD

NPB

The hole transport layer 14 may have a thickness of about 50 Å to about 1000 Å, for example, a thickness of about 100 Å to about 800 Å. When the thickness of the hole transport layer 14 is within the above ranges, the hole transport layer 14 may have satisfactory hole transport characteristics without an increase in driving voltage.

The emission layer 15 may be formed on the hole transport layer 14 by, e.g., vacuum deposition, wet process, or laser transferring.

When the emission layer 15 is formed by vacuum deposition or spin coating, the deposition or coating conditions may be similar to those applied to form the hole injection layer 13, although the deposition or coating conditions may vary according to the material that is used to form the emission layer 15.

The emission layer 15 may be the first layer including the heterocyclic compound represented by Formula 1 described above. The emission layer 15 may further include, in addition to the heterocyclic compound represented by Formula 1, a known phosphorescent host, fluorescent host, phosphorescent dopant, or fluorescent dopant. The heterocyclic compound represented by Formula 1 may function as a phosphorescent host, a fluorescent host, a phosphorescent dopant, or a fluorescent dopant.

As a known host, 4,4'-N,N'-dicarbazole-biphenyl (CBP), 9,10-di-naphthalene-2-yl-anthracene (ADN, a structure thereof is illustrated below), TPBI (a structure thereof is illustrated below), TBADN (a structure thereof is illustrated below), E3 (a structure thereof is illustrated below), etc. may be used, but are not limited thereto.

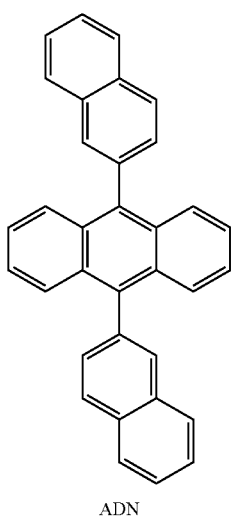

ADN

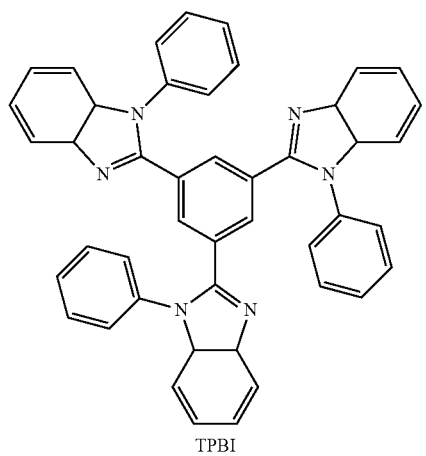

TPBI

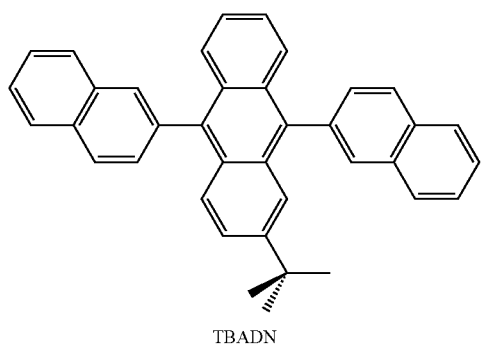

TBADN

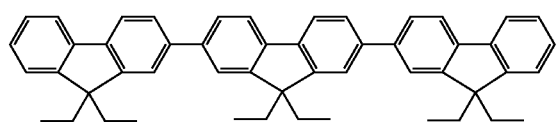

E3

As a red dopant, PtOEP (a structure thereof is illustrated below), Ir(piq)₃ (a structure thereof is illustrated below), Btp₂Ir(acac) (a structure thereof is illustrated below), etc. may be used, but are not limited thereto.

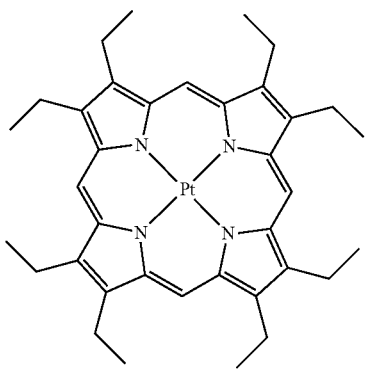

PtOEP

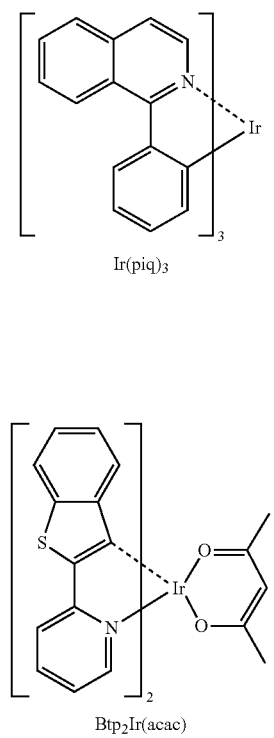

Ir(piq)₃

Btp₂Ir(acac)

Also, as a green dopant, Ir(ppy)₃ (ppy=phenyl pyridine, a structure thereof is illustrated below), Ir(ppy)₂(acac) (a structure thereof is illustrated below), Ir(mpyp)₃ (a structure thereof is illustrated below), etc. may be used, but are not limited thereto.

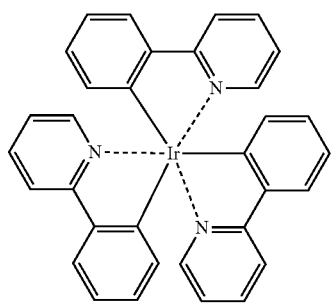

Ir(ppy)₃

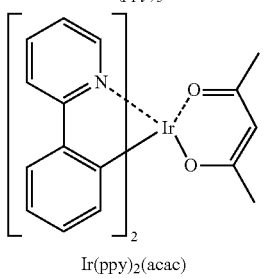

Ir(ppy)₂(acac)

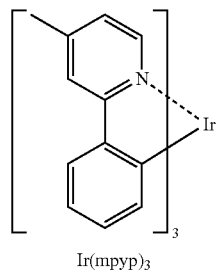

Ir(mpyp)₃

As a blue dopant, F₂Irpic (a structure thereof is illustrated below), (F₂ppy)₂Ir(tmd) (a structure thereof is illustrated below), Ir(dfppz)₃ (a structure thereof is illustrated below), DPVBi (a structure thereof is illustrated below), 4,4'-bis(4-diphenyl aminostaryl)biphenyl (DPAVBi, a structure thereof is illustrated below), 2,5,8,11-tetra-tert-butyl perylene (TBPe, a structure thereof is illustrated below), etc. may be used, but are not limited thereto.

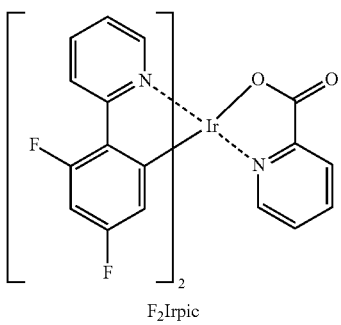

F₂Irpic

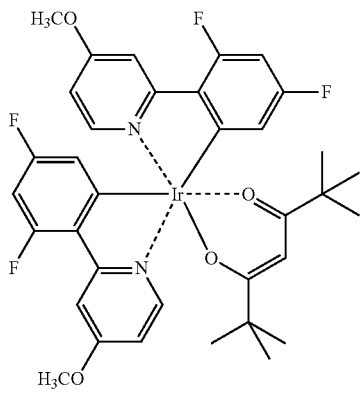

(F2ppy)2Ir(tmd)

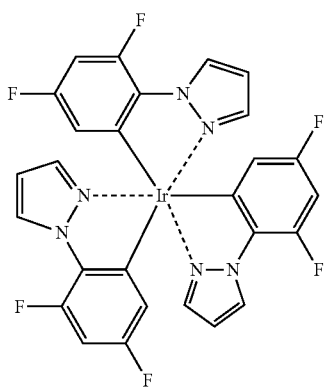

Ir(dfppz)₃

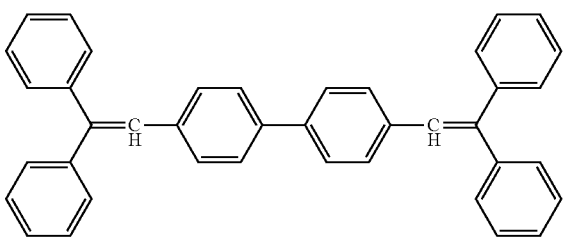

DPVBi

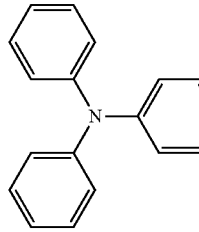

DPAVBi

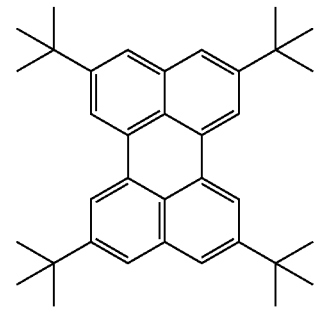

TBPe

If the emission layer 15 includes a host and a dopant, an amount of the dopant may be from about 0.01 to about 15 parts by weight based on about 100 parts by weight of the host, but are not limited thereto.

A thickness of the emission layer 15 may be from about 100 Å to about 1000 Å, for example, about 200 Å to about 600 Å. If the thickness of the emission layer 15 is within these ranges, excellent luminescence characteristics may be obtained without a substantial increase in driving voltage.

If the emission layer 15 includes a phosphorescent dopant, a hole blocking layer (HBL) (not shown in FIG. 1) may be formed between the electron transport layer 16 and the emission layer 15 by vacuum deposition, wet process, or laser transferring, to prevent diffusion of a triple exciton or a hole into the electron transport layer 16. If the HBL is formed by vacuum deposition or spin coating, the deposition or coating conditions may be similar to those applied to form the hole injection layer 13, although the deposition or coating conditions may vary according to the material that is used to form the HBL. As a HBL material, any one of known hole blocking materials may be used, and examples thereof are an oxadiazole derivative, a triazole derivative, a phenanthroline derivative, etc.

A thickness of the HBL may be from about 50 Å to about 1000 Å, for example, about 100 Å to about 300 Å. If the thickness of the HBL is within the ranges described above, excellent hole blocking characteristics may be obtained without a substantial increase in driving voltage.

Then, the electron transport layer 16 may be formed by using various methods, such as the vacuum deposition, wet process, laser transferring, etc., as described above. As an electron transport layer material, the heterocyclic compound represented by Formula 1 described above may be used. Also, known electron transporting materials may instead be used, and examples thereof are a quinoline derivative, such as tris (8-quinolinolate)aluminum (Alq3), TAZ (a structure thereof is illustrated below), BAlq (a structure thereof is illustrated below), and beryllium bis(benzoquinolin-10-olate (Bebq2), but are not limited thereto.

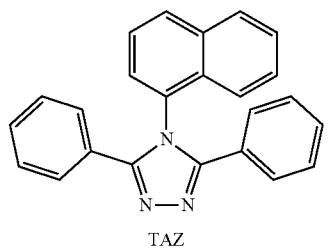

TAZ

-continued

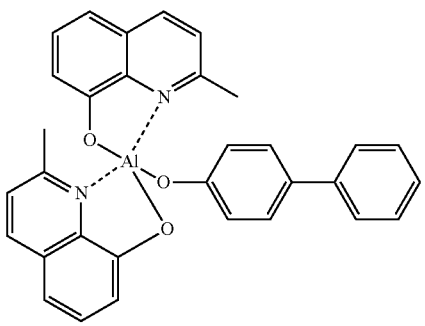

BAlq

The electron transport layer 16 may include an electron transporting organic compound and a metal-containing compound. Nonlimiting examples of the electron transporting organic compound are (9,10-di(naphthalene-2-yl)anthracene (ADN); and anthracene-based compounds, such as compounds 201 and 202 below.

<Compound 201>

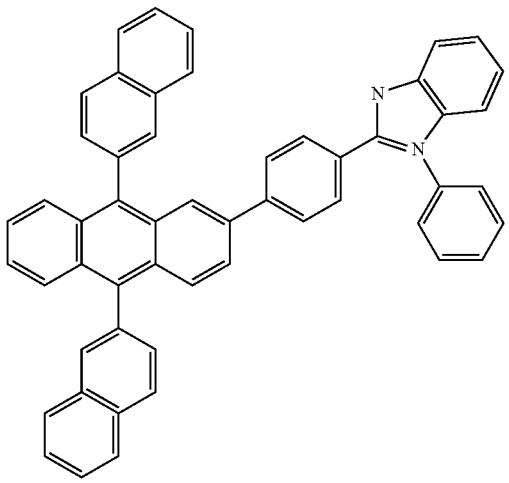

<Compound 202>

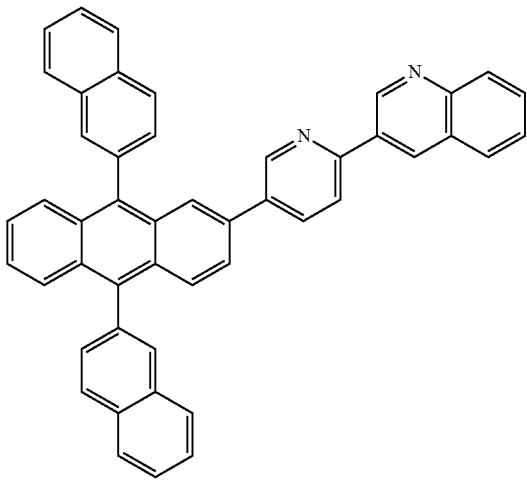

The metal-containing compound may include a Li complex. Non-limiting examples of the Li complex may include lithium quinolate (LiQ), Compound 203 below, etc.:

<Compound 203>

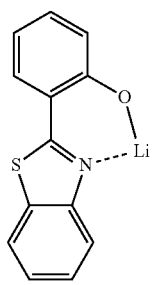

A thickness of the electron transport layer 16 may be from about 100 Å to about 1000 Å, for example, about 150 Å to about 500 Å. If the thickness of the electron transport layer 16 is within the ranges described above, excellent electron transporting characteristics may be obtained without a substantial increase in driving voltage. If the electron transport layer 16 is formed by vacuum deposition or spin coating, the deposition or coating conditions may be similar to those applied to form the hole injection layer 13, although the deposition or coating conditions may vary according to the material that is used to form the electron transport layer 16.

The electron injection layer 17 may be deposited on the electron transport layer 16 by using a material that facilitates injection of electrons from an anode. As a material for forming the electron injection layer 17, any suitable electron injection layer material, e.g., LiF, NaCl, CsF, Li$_2$O, or BaO, may be used. The deposition conditions of the electron injection layer 17 may be similar to those applied to form the hole injection layer 13, although the deposition or coating conditions may vary according to the material that is used to form the electron injection layer 17.

A thickness of the electron injection layer 17 may be from about 1 Å to about 100 Å, e.g., about 3 Å to about 90 Å. Maintaining the thickness of the electron injection layer 17 within the ranges described above may help ensure that excellent electron injection characteristics are obtained without a substantial increase in driving voltage.

The second electrode 18 may be formed as a reflection electrode on the electron injection layer 17. The second electrode 18 may be a cathode as an electron injection electrode, and in this case, a low work function metal, alloy, electrically conductive compound, and a mixture thereof may be used as a second electrode metal. For example, lithium (Li), magnesium (Mg), aluminum (Al), aluminum-lithium (Al—Li), calcium (Ca), magnesium-indium (Mg—In), magnesium-silver (Mg—Ag), etc. may be formed as a thin film for use as a reflection electrode. Also, if the organic light-emitting diode is used in a top-emission light-emitting device, a transmission electrode may be formed using ITO or IZO.

The organic light-emitting diode may be included in a flat display device including a transistor. Accordingly, an embodiment of the present invention provides a flat display device including: a transistor including a source, a drain, a gate, and an active layer, and the organic light-emitting diode described above, wherein the source or the drain is electrically connected to the first electrode of the organic light-emitting diode. The active layer of the transistor may be an amorphous silicon layer, a crystalloid silicon layer, an organic semiconductor layer, or an oxide semiconductor layer, and is not limited thereto.

Hereinafter, an organic light-emitting diode according to an embodiment of the present invention will be described in detail with reference to Synthesis Examples and Examples regarding Compounds 7, 10, 21, 24, 26, 27, 30, 33, 39, 40, 43, 52, 58, 72, 81, 107, 11025, 31, 41, and 11157. The following Examples and Comparative Examples are provided in order to set forth particular details of one or more embodiments. However, it will be understood that the embodiments are not limited to the particular details described. Further, the Comparative Examples are set forth to highlight certain characteristics of certain embodiments, and are not to be construed as either limiting the scope of the invention as exemplified in the Examples or as necessarily being outside the scope of the invention in every respect.

EXAMPLE

Synthesis Example of Compound 7

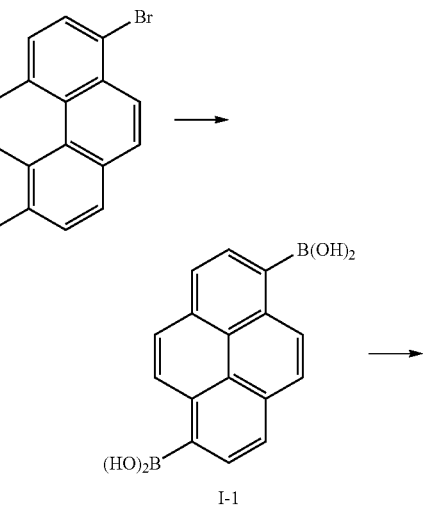

I-1

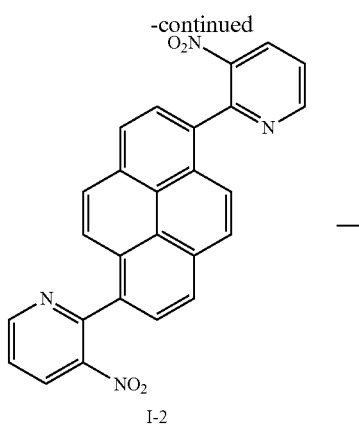

I-2

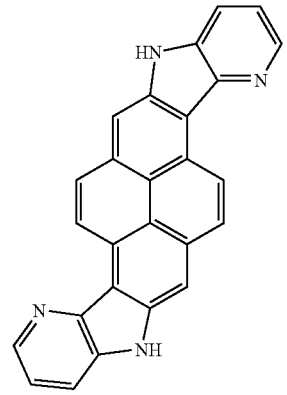

I-3

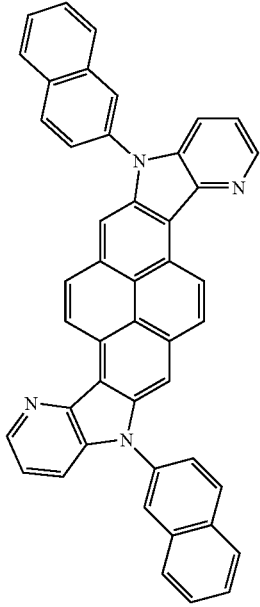

7

Synthesis of Intermediate I-1

7.20 g (20.0 mmol) of 1,6-dibromopyrene was molten in 60 mL of THF and then 16.0 mL (2.5M in Hexane, 40.0 mmol) of normal butyllithium was slowly dropped thereto at a temperature of −78° C. At the same temperature, the mixture was stirred for one hour and then B(OiPr)$_3$ 18.44 mL (80.0 mmol) was slowly added thereto. A temperature of a reaction solution was slowly increased to room temperature for 3 hours, and then 50 mL of water was added thereto and the resultant solution was extracted three times with 50 mL of ethyl ether. A collected organic layer was dried using magnesium sulfate, and the residual obtained by removing the used solvent therefrom by evaporation was recrystallized to obtain Intermediate I-1, 4.35 g (Yield: 75%). The formed compound was confirmed by liquid chromatography-mass spectroscopy (LC-MS). $C_{16}H_{12}B_2O_4$: M+ 290.1

Synthesis of Intermediate I-2

2.90 g (10.0 mmol) of Intermediate I-1, 4.06 g (20.0 mmol) of 2-bromo-3-nitropyridine, 1.15 g (1.0 mmol) of Pd(PPh$_3$)$_4$, and 8.29 g (60.0 mmol) of K$_2$CO$_3$ were dissolved in 60 ml of THF/H$_2$O (2/1) mixed solution, and then the mixture was stirred at a temperature of 70° C. for 5 hours. A reaction solution was cooled to room temperature and then 40 mL of water was added thereto and the resultant solution was extracted three times with 50 mL of ethyl ether. A collected organic layer was dried using magnesium sulfate, and the residual obtained by removing the used solvent therefrom by evaporation was separation purified by silica gel chromatography to obtain Intermediate I-2, 3.44 g (Yield: 77%). The formed compound was confirmed by LC-MS. $C_{26}H_{14}N_4O_4$: M+ 446.1

Synthesis of Intermediate I-3

4.46 g (10.0 mmol) of Intermediate I-2 and 11.02 g (42 mmol) of triphenylphosphine (PPh$_3$) were dissolved in 50 ml of 1,2-dichlorobenzene and then stirred at a temperature of 170° C. for 12 hours. A reaction solution was cooled to room temperature, and then the solvent used was removed therefrom under vacuum conditions and the resultant solution was extracted three times with 50 mL of water and 50 mL of dichloromethane. A collected organic layer was dried using magnesium sulfate, and the residual obtained by removing the used solvent therefrom by evaporation was separation purified by silica gel column chromatography to obtain 2.49 g (Yield: 65%) of Intermediate I-3. The formed compound was confirmed by LC-MS. $C_{26}H_{14}N_4$: M+ 382.1

Synthesis of Compound 7

3.82 g (10.0 mmol) of Intermediate I-3, 6.21 g (30.0 mmol) of 2-bromonaphthalene, 0.38 g (2.0 mmol) of CuI, 0.1 g (0.4 mmol) of 18-Crown-6, and 8.30 g (60.0 mmol) of K$_2$CO$_3$ were dissolved in 40 ml of 1,3-dimethyl-3,4,5,6-tetrahydro-2(1H)-pyrimidinone (DMPU) and then the mixture was stirred at a temperature of 170° C. for 12 hours. A reaction solution was cooled to room temperature, and extracted three times with 50 mL of water and 50 mL of dichloromethane. A collected organic layer was dried using magnesium sulfate, and the residual obtained by removing the used solvent therefrom by evaporation was separation purified by silica gel column chromatography to obtain 4.82 g (Yield: 76%) of Compound 7. The formed compound was confirmed by LC-MS and NMR. $C_{46}H_{26}N_4$: M+ 634.2

$^1$H NMR (CDCl$_3$, 400 MHz) δ (ppm) 8.57 (d, 2H), 8.52 (dd, 2H), 8.42 (d, 2H), 8.21 (s, 2H), 8.03 (d, 2H), 7.88 (d, 2H), 7.77-7.72 (m, 2H), 7.71-7.65 (m, 4H), 7.59-7.49 (m, 6H), 7.04 (dd, 2H)

Synthesis Example of Compound 10

3.46 g (Yield: 80%) of Compound 10 was prepared using Intermediate I-3 and 3-iodo-9-phenylcarbazolein in the same manner as used to synthesize Compound 7. The formed compound was confirmed by LC-MS and NMR. $C_{62}H_{36}N_6$: M+ 864.3

$^1$H NMR (CDCl$_3$, 400 MHz) δ (ppm) 8.47 (d, 2H), 8.54-8.51 (m, 2H), 8.46 (d, 2H), 8.19 (s, 2H), 8.14-8.11 (m, 4H), 7.68 (dd, 2H), 7.59 (d, 2H), 7.51-7.47 (m, 8H), 7.38-7.30 (m, 8H), 7.15-7.13 (m, 2H), 7.03 (dd, 2H)

Synthesis Example of Compound 25

3.39 g (Yield: 78%) of Compound 25 was prepared using Intermediate I-3 and 4-bromotriphenylamine in the same manner as used to synthesize Compound 7. The formed compound was confirmed by LC-MS and NMR. C$_{62}$H$_{40}$N$_6$: M+ 868.3

$^1$H NMR (CDCl$_3$, 400 MHz) δ (ppm) 8.58-8.51 (m, 4H), 8.42 (d, 2H), 8.22 (s, 2H), 7.95-7.91 (m, 4H), 7.69 (dd, 2H), 7.43-7.39 (m, 8H), 7.26-7.22 (m, 2H), 7.04-7.00 (m, 4H), 6.85-6.81 (m, 4H), 6.60-6.58 (m, 8H)

Synthesis Example of Compound 31

2.79 g (Yield: 66%) of Compound 31 was prepared using Intermediate I-3 and 2-chloro-4,6-diphenyl-1,3,5-triazine in the same manner as used to synthesize Compound 7. The formed compound was confirmed by LC-MS and NMR. C$_{56}$H$_{32}$N$_{10}$: M+ 844.3

$^1$H NMR (CDCl$_3$, 400 MHz) δ (ppm) 8.96 (s, 2H), 8.59-8.52 (m, 12H), 8.42 (d, 2H), 8.25 (dd, 2H), 7.45-7.37 (m, 12H), 7.16-7.12 (m, 2H)

Synthesis Example of Compound 21

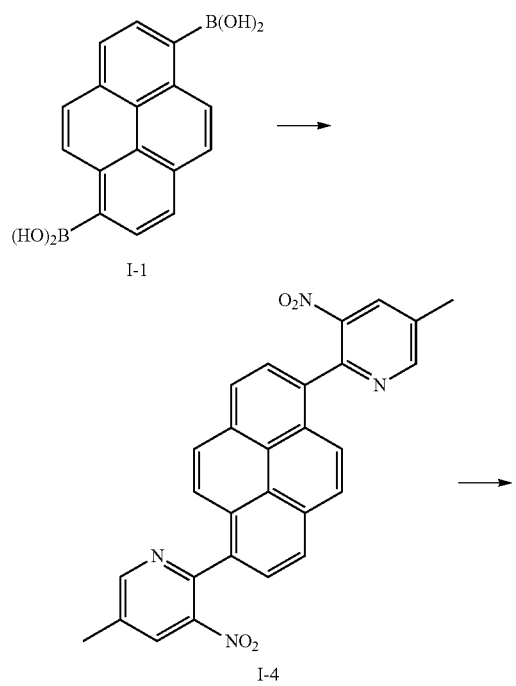

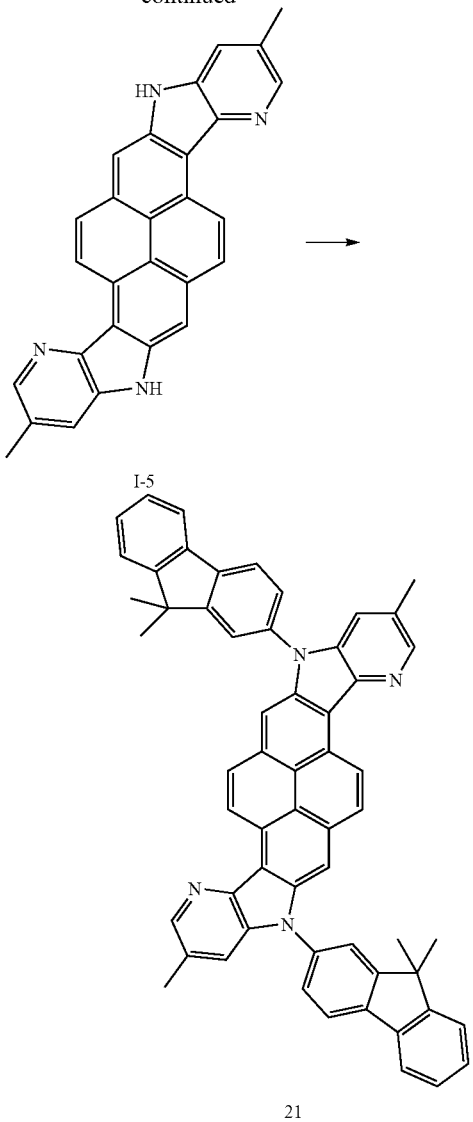

Synthesis of Intermediate I-4

3.56 g (Yield: 75%) of Intermediate I-4 was prepared using Intermediate I-1 and 2-bromo-5-methyl-3-nitropyridine in the same manner as used to synthesize Intermediate I-2. The formed compound was confirmed by LC-MS. C$_{28}$H$_{18}$N$_4$O$_4$: M+ 474.1

Synthesis of Intermediate I-5

2.71 g (Yield: 66%) of Intermediate I-5 was prepared using Intermediate I-4 and triphenylphosphine in the same manner as used to synthesize Intermediate I-3. The formed compound was confirmed by LC-MS. C$_{28}$H$_{18}$N$_4$: M+ 410.2

Synthesis of Compound 21

2.82 g (Yield: 71%) of Compound 21 was prepared using Intermediate I-5 and 2-bromo-9,9-dimethylfluorene in the same manner as used to synthesize Compound 7. The formed compound was confirmed by LC-MS and NMR. C$_{58}$H$_{42}$N$_4$: M+ 794.3

$^1$H NMR (CDCl$_3$, 400 MHz) δ (ppm) 8.64-8.63 (m, 2H), 8.57 (d, 2H), 8.42 (d, 2H), 8.17 (s, 2H), 7.82-7.80 (m, 2H), 7.71-7.66 (m, 4H), 7.53-7.51 (m, 2H), 7.34-7.31 (m, 2H), 7.07-7.03 (m, 2H), 6.91 (dd, 2H), 6.74-6.72 (m, 2H), 2.56 (s, 6H), 1.85 (s, 12H)

Synthesis Example of Compound 24

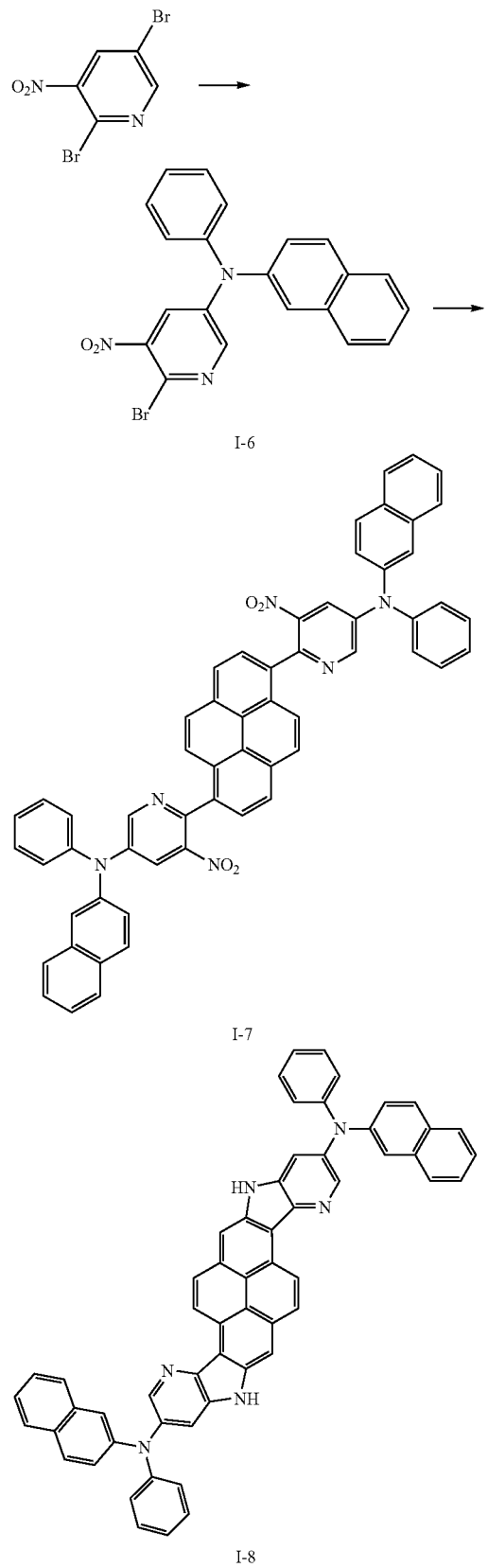

I-6

I-7

I-8

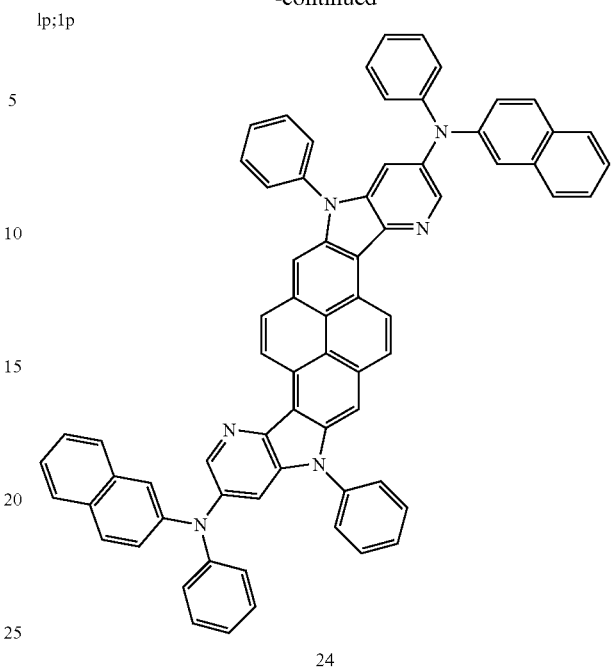

24

Synthesis of Intermediate I-6

16.91 g (60.0 mmol) of 2,5-dibromo-3-nitropyridine, 4.38 g (20.0 mmol) of N-phenyl-2-naphthylamine, 0.37 g (0.4 mmol) of $Pd_2(dba)_3$, 0.08 g (0.4 mmol) of $P(tBu)_3$, and NaOtBu 2.88 g (30.0 mmol) were molten in 100 mL of toluene and then the mixture was heated at a temperature of 85° C. for 5 hours while heating. A reaction solution was cooled to room temperature, and then extracted three times with 80 mL of water and 80 mL of diethylether. A collected organic layer was dried using magnesium sulfate, and the residual obtained by removing the used solvent therefrom by evaporation was separation purified by silica gel column chromatography to obtain Intermediate I-6, 3.87 g (Yield: 46%). The formed compound was confirmed by LC-MS. $C_{21}H_{14}BrN_3O_2$: M+ 419.0

Synthesis of Intermediate I-7

6.43 g (Yield: 73%) of Intermediate I-7 was prepared using Intermediate I-1 and Intermediate I-6 in the same manner as used to synthesize Intermediate I-2. The formed compound was confirmed by LC-MS. $C_{58}H_{36}N_6O_4$: M+ 880.3

Synthesis of Intermediate I-8

5.79 g (Yield: 71%) of Intermediate I-8 was prepared using Intermediate I-7 and triphenylphosphine in the same manner as used to synthesize Intermediate I-3. The formed compound was confirmed by LC-MS. $C_{58}H_{36}N_6$: M+ 816.3

Synthesis of Compound 24

4.12 g (Yield: 85%) of Compound 24 was prepared using Intermediate I-8 and iodobenzene in the same manner as used to synthesize Compound 7. The formed compound was confirmed by LC-MS and NMR. $C_{70}H_{44}N_6$: M+ 968.4

$^1$H NMR (CDCl$_3$, 400 MHz) δ (ppm) 8.56 (d, 2H), 8.45 (d, 2H), 8.33 (s, 2H), 8.26 (dd, 2H), 7.98 (d, 2H), 7.77-7.54 (m, 16H), 7.42-7.33 (m, 10H), 7.17 (dd, 2H), 6.84-6.82 (m, 2H), 6.61-6.59 (m, 4H)

Synthesis Example of Compound 41

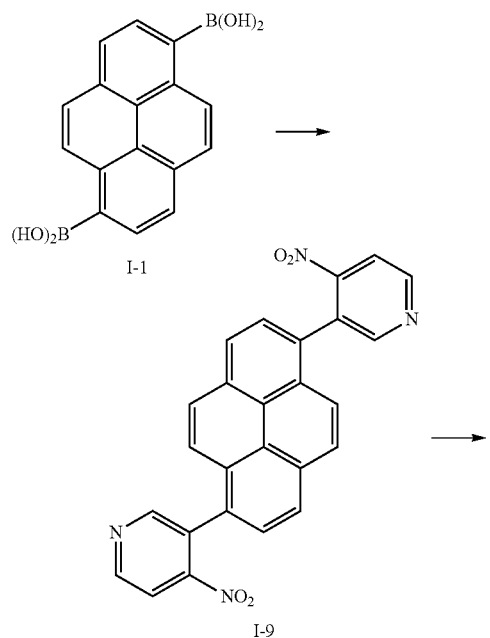

Synthesis of Intermediate I-9

3.53 g (Yield: 79%) of Intermediate I-8 was prepared using Intermediate I-1 and 3-bromo-4-nitropyridine in the same manner as used to synthesize Intermediate I-2. The formed compound was confirmed by LC-MS. $C_{26}H_{14}N_4O_4$: M+ 446.1

Synthesis of Intermediate I-10

2.94 g (Yield: 77%) of Intermediate I-10 was prepared using Intermediate I-9 and triphenylphosphine in the same manner as used to synthesize Intermediate I-3. The formed compound was confirmed by LC-MS. $C_{26}H_{14}N_4$: M+ 382.1

Synthesis of Compound 41

3.37 g (Yield: 78%) of Compound 41 was prepared using Intermediate I-10 and 9-(4-bromophenyl)-9H-carbazole in the same manner as used to synthesize Compound 7. The formed compound was confirmed by LC-MS and NMR. $C_{62}H_{36}N_6$: M+ 864.3

$^1$H NMR (CDCl$_3$, 400 MHz) δ (ppm) 9.42 (s, 2H), 9.03 (d, 2H), 8.30-8.21 (m, 6H), 8.10-8.08 (m, 4H), 7.86-7.74 (m, 8H), 7.57 (d, 2H), 7.37-7.32 (m, 8H), 7.26-7.20 (m, 4H)

Synthesis Example of Compound 57

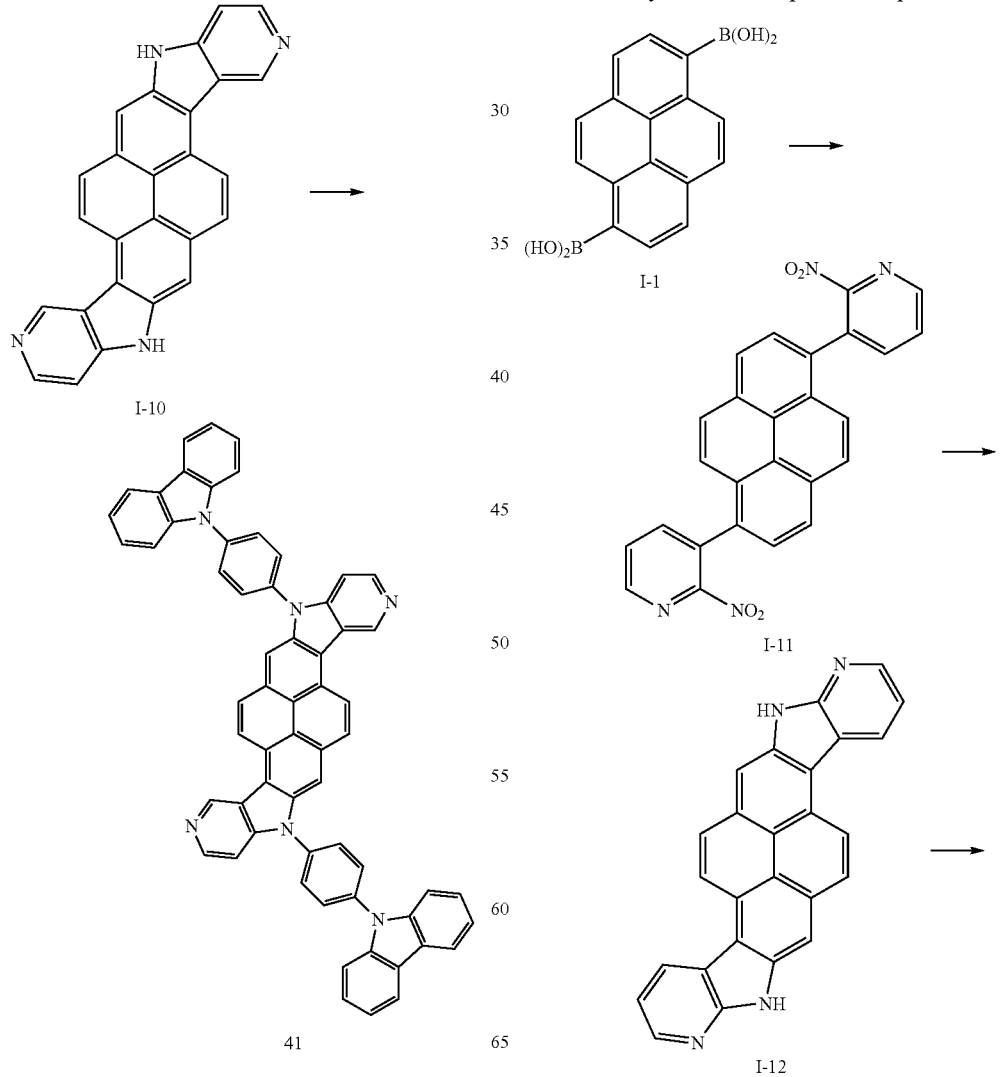

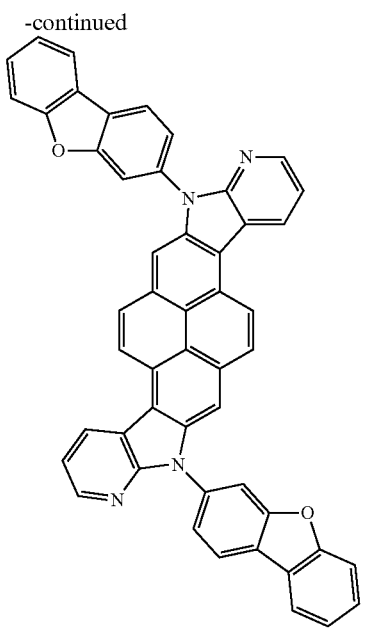

57

Synthesis of Intermediate I-11

3.39 g (Yield: 76%) of Intermediate I-11 was prepared using Intermediate I-1 and 3-bromo-2-nitropyridine in the same manner as used to synthesize Intermediate I-2. The formed compound was confirmed by LC-MS. $C_{26}H_{14}N_4O_4$: M+ 446.1

Synthesis of Intermediate I-12

2.87 g (Yield: 75%) of Intermediate I-12 was prepared using Intermediate I-11 and triphenylphosphine in the same manner as used to synthesize Intermediate I-3. The formed compound was confirmed by LC-MS. $C_{26}H_{14}N_4$: M+ 382.1

Synthesis of Compound 57

2.36 g (Yield: 66%) of Compound 57 was prepared using Intermediate I-12 and 3-bromodibenzo[b,d]furan in the same manner as used to synthesize Compound 7. The formed compound was confirmed by LC-MS and NMR. $C_{50}H_{26}N_4O_2$: M+ 714.2

$^1$H NMR (CDCl$_3$, 400 MHz) δ (ppm) 9.11 (d, 2H), 8.56 (dd, 2H), 8.49-8.46 (m, 4H), 8.21-8.19 (m, 2H), 8.10 (d, 2H), 7.99-7.96 (m, 2H), 7.84 (d, 2H), 7.63-7.55 (m, 6H), 7.45-7.41 (m, 2H), 7.26-7.23 (m, 2H)

Example 1

As an anode, 15 Ω/cm$^2$ (1200 Å) ITO glass substrate manufactured by Corning Co., Ltd was cut to a size of 50 mm×50 mm×0.7 mm and sonicated with isopropyl alcohol and pure water each for 5 minutes, and then a ultraviolet ray was irradiated thereto for 30 minutes, followed by exposure to ozone. Then, the resultant ITO glass substrate was installed in a vacuum deposition device. 2-TNATA was vacuum deposited on the ITO glass substrate to form a hole injection layer having a thickness of 600 Å, and 4,4'-bis[N-(1-naphthyl)-N-phenyl amino]biphenyl (NPB) was vacuum deposited on the hole injection layer to form a hole transport layer having a thickness of 300 Å.

Compound 7 as a green fluorescent host and C545T as a green fluorescent dopant were co-deposited on the hole transport layer at a weight ratio of 98:2 to form an emission layer having a thickness of 300 Å.

Subsequently, Alq$_3$ was vacuum deposited on the emission layer to form an electron transport layer having a thickness of 300 Å. LiF was deposited on the electron transport layer to form an electron injection layer having a thickness of 10 Å and then, Al was vacuum deposited thereon to form an electrode having a thickness of 3000 Å, thereby forming a structure of LiF/Al electrode, thereby completing the manufacture of an organic light-emitting diode.

Example 2

An organic light-emitting diode was manufactured in the same manner as in Example 1, except that the emission layer was formed using Compound 10 instead of Compound 7.

Example 3

An organic light-emitting diode was manufactured in the same manner as in Example 1, except that the emission layer was formed using Compound 21 instead of Compound 7.

Example 4

An organic light-emitting diode was manufactured in the same manner as in Example 1, except that the emission layer was formed using Compound 41 instead of Compound 7.

Example 5

An organic light-emitting diode was manufactured in the same manner as in Example 1, except that the emission layer was formed using Compound 57 instead of Compound 7.

Example 6

An organic light-emitting diode was manufactured in the same manner as in Example 1, except that the emission layer was formed using Alq$_3$ instead of Compound 7 as the green fluorescent host and Compound 24 instead of C545T as the green fluorescent dopant.

Example 7

An organic light-emitting diode was manufactured in the same manner as in Example 6, except that the emission layer was formed using Compound 25 instead of Compound 24.

Example 8

An organic light-emitting diode was manufactured in the same manner as in Example 1, except that the emission layer was formed using Alq$_3$ instead of Compound 7 as the green fluorescent host and C545T as the green fluorescent dopant, and the electron transport layer was formed using Compound 31 instead of Alq$_3$ on the emission layer.

Example 9

An organic light-emitting diode was manufactured in the same manner as in Example 1, except that the emission layer was formed using Compound 10 instead of Compound 7 as the green fluorescent host and Compound 24 instead of C545T as the green fluorescent dopant, and the electron transport layer was formed using Compound 31 instead of Alq$_3$ on the emission layer.

Comparative Example 1

An organic light-emitting diode was manufactured in the same manner as in Example 1, except that the emission layer was formed using $Alq_3$ instead of Compound 7 as the green fluorescent host.

Evaluation Example

The current density, driving voltage, brightness, luminescence efficiency, emission color, and half lifetime (a time for which brightness is decreased in half (50%) at a current density of 100 mA/cm$^2$) of each of the organic light-emitting diodes manufactured according to Examples 1 to 9, and the organic light-emitting diode manufactured according to Comparative Example 1 were measured by using PR650 (Spectroscan) Source Measurement Unit (product of Photo-Research Co., Ltd), and results thereof are shown in Table 1 below.

TABLE 1

|  | Light-emitting material or electron transporting material | Driving voltage (V) | Current density (mA/cm$^2$) | Brightness (cd/m$^2$) | Luminescence efficiency (cd/A) | Emission color | Lifetime (h) |
| --- | --- | --- | --- | --- | --- | --- | --- |
| Example 1 | Compound 7 | 6.35 | 50 | 8,450 | 16.9 | green | 550 |
| Example 2 | Compound 10 | 6.15 | 50 | 8,850 | 17.7 | green | 572 |
| Example 3 | Compound 21 | 6.31 | 50 | 8,750 | 17.5 | green | 495 |
| Example 4 | Compound 41 | 6.20 | 50 | 8,550 | 17.1 | green | 565 |
| Example 5 | Compound 57 | 6.17 | 50 | 8,150 | 16.3 | green | 430 |
| Example 6 | Compound 24 | 7.12 | 50 | 9,850 | 19.7 | green | 460 |
| Example 7 | Compound 25 | 7.15 | 50 | 9,300 | 18.6 | green | 472 |
| Example 8 | Compound 31 | 5.72 | 50 | 7,800 | 15.6 | green | 390 |
| Example 9 | Compound 10 Compound 24 Compound 31 | 5.65 | 50 | 10,600 | 21.2 | green | 534 |
| Comparative Example 1 | $Alq_3$ | 7.45 | 50 | 6,102 | 12.2 | green | 237 |

Referring to Table 1 above, it may be seen that when the heterocyclic compound represented by Formula 1 was used as an emission layer material (host, dopant) or an electron transport layer material of an organic light-emitting diode, the driving voltage of the corresponding organic light-emitting diodes was decreased by about 1 V compared to when $Alq_3$ and C545T as known materials were used, and also, efficiency of the organic light-emitting diodes manufactured according to Examples 1 to 21 was substantially increased.

For example, it may be seen that in comparison with Comparative Example 1, the driving voltages of the organic light-emitting diodes manufactured according to Examples 1 to 5 in which the heterocyclic compound represented by Formula 1 was used as a host were decreased by about 1 V or more, and efficiency and lifetime thereof were also improved; efficiencies of the organic light-emitting diodes manufactured according to Examples 6 and 7 in which the heterocyclic compound represented by Formula 1 was used as a dopant were increased by 150% or more, and lifetimes thereof were also increased by about 200%; an driving voltage of the organic light-emitting diode manufactured according to Example 8 in which the heterocyclic compound represented by Formula 1 was used as the electron transporting material were decreased by about 1.5 V or more. Also, the driving voltage of the organic light-emitting diode manufactured according to Example 9 in which the heterocyclic compound represented by Formula 1 was used as a host or dopant of an emission layer, or as an electron transporting material were decreased by about 1.8 V compared to Comparative Example 1, and efficiency thereof was increased by about 200% and lifetime thereof was increased by 200% or more.

From the results described above, it may be seen that a light-emitting diode including the heterocyclic compound represented by Formula 1 device has a low driving voltage, high luminescence efficiency, and long lifetime.

The heterocyclic compound represented by Formula 1 may exhibit excellent emission characteristics and charge transport characteristics. An organic light-emitting diode including the heterocyclic compound represented by Formula 1 may have a low driving voltage, high luminescence efficiency, and long lifetime, and thus a flat display device including the organic light-emitting diode may have excellent performance.

While the present invention has been particularly shown, and described with reference to exemplary embodiments thereof, it will be understood by those of ordinary skill in the art that various changes in form, and details may be made therein without departing from the spirit, and scope of the present invention as defined by the following claims.

What is claimed is:

1. A heterocyclic compound represented by Formula 1 below:

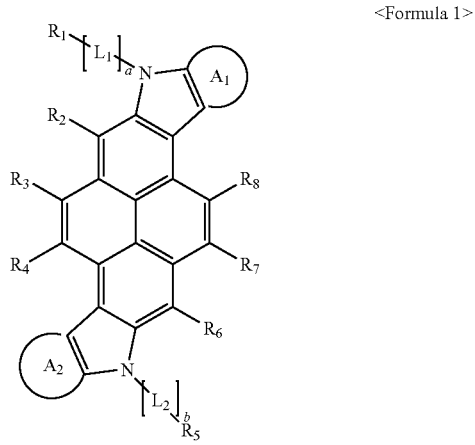

<Formula 1> wherein:
$A_1$ and $A_2$ are each independently a substituted or unsubstituted fused pyridine cycle, $R_1$ to $R_8$ are each independently a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cyclo alkyl group, a substituted or unsubstituted $C_3$-$C_{30}$ cyclo alkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_3$-$C_{30}$ hetero aryl group, or a group represented by $N(Q_1)(Q_2)$, wherein $Q_1$, and $Q_2$ are each independently a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cyclo alkyl group, a substituted or unsubstituted $C_3$-$C_{30}$ cyclo alkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, or a substituted or unsubstituted $C_3$-$C_{30}$ hetero aryl group, $L_1$ and $L_2$ are each independently a substituted or unsubstituted $C_6$-$C_{30}$ arylene group or a substituted or unsubstituted $C_3$-$C_{30}$ heteroarylene group, and a and b are each independently an integer of 0 to 3.

2. The heterocyclic compound as claimed in claim 1, wherein:

$A_1$ and $A_2$ are each independently a group represented by one of Formulae 2A to 2D, below:

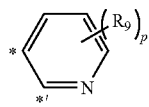

<Formula 2A>

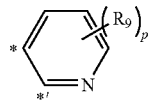

<Formula 2B>

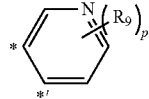

<Formula 2C>

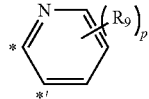

<Formula 2D>

$R_9$ is independently a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cyclo alkyl group, a substituted or unsubstituted $C_3$-$C_{30}$ cyclo alkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_3$-$C_{30}$ hetero aryl group, or a group represented by $N(Q_3)(Q_4)$, in which $Q_3$ and $Q_4$ are each independently a hydrogen atom, a deuterium atom, a halogen atom, a hydroxyl group, a cyano group, an amino group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cyclo alkyl group, a substituted or unsubstituted $C_3$-$C_{30}$ cyclo alkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, or a substituted or unsubstituted $C_3$-$C_{30}$ hetero aryl group, p is an integer from 1 to 3, and

* and *' are sites for fusing.

3. The heterocyclic compound as claimed in claim 1, wherein:

$A_1$ and $A_2$ are each independently a group represented by one of Formulae 3AA to 3BB, below:

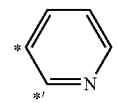

<Formula 3AA>

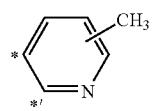

<Formula 3AB>

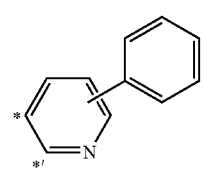

<Formula 3AC>

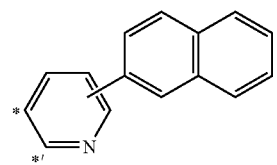

<Formula 3AD>

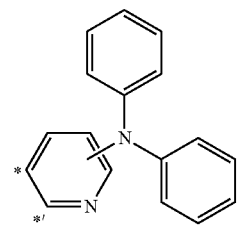

<Formula 3AE>

<Formula 3AF>

<Formula 3AG>

<Formula 3AH>

<Formula 3AI>

<Formula 3AJ>

<Formula 3AK>

<Formula 3AL>

<Formula 3AM>

<Formula 3AN>

<Formula 3AO>

<Formula 3AP>

<Formula 3AQ>

<Formula 3AR>

<Formula 3AS>

<Formula 3AT>
<Formula 3AU>
<Formula 3AV>
<Formula 3AW>
<Formula 3AX>
<Formula 3AY>
<Formula 3AZ>
<Formula 3BA>
<Formula 3BB> and
* and *' are sites for fusing.

4. The heterocyclic compound as claimed in claim 1, wherein $R_1$ to $R_8$ are each independently a hydrogen atom, a deuterium atom, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted non-phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted fluorenyl group, a substituted or unsubstituted spirofluorenyl group, a substituted or unsubstituted phenalenyl group, a substituted or unsubstituted phenanthrenyl group, a substituted or unsubstituted phenanthridinyl group, a substituted or unsubstituted phenanthrollinyl group, a substituted or unsubstituted anthryl group, a substituted or unsubstituted fluorantenyl group, a substituted or unsubstituted triphenylenyl group, a substituted or unsubstituted pyrenyl group, a substituted or unsubstituted chricenyl group, a substituted or unsubstituted naphthacenyl group, a substituted or unsubstituted pycenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted benzoimidazolyl group, a substituted or unsubstituted pyrazolyl group, a substituted or unsubstituted pyridinyl group, a substituted or unsubstituted imidazopyridinyl group, a substituted or unsubstituted pyrazinyl group, a substituted or unsubstituted pyrimidinyl group, a substituted or unsubstituted imidazopyrimidinyl group, a substituted or unsubstituted pyridazinyl group, a substituted or unsubstituted indolyl group, a substituted or unsubstituted isoindolyl group, a substituted or unsubstituted pyrido indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthallazinyl group, a substituted or unsubstituted naphthyridinyl group, a substituted or unsubstituted quinoxalinyl group, a substituted or unsubstituted quinazolinyl group, a substituted or unsubstituted carbazolyl group, a substituted or unsubstituted phenazinyl group, a substituted or unsubstituted puranyl group, a substituted or unsubstituted benzopuranyl group, a substituted or unsubstituted dibenzopuranyl group, a substituted or unsubstituted thiophenyl group, a substituted or unsubstituted benzothiophenyl group, a substituted or unsubstituted dibenzothiophenyl group, a substituted or unsubstituted thiazolyl group, a substituted or unsubstituted isothiazolyl group, a substituted or unsubstituted benzothiazolyl group, a substituted or unsubstituted oxazolyl group, a substituted or unsubstituted benzooxazolyl group, a substituted or unsubstituted isooxazolyl group, a substituted or unsubstituted oxadiazolyl group, a substituted or unsubstituted triazolyl group, a substituted or unsubstituted triazinyl group, a substituted or unsubstituted tetrazolyl group, or a group represented by $N(Q_1)(Q_2)$, wherein $Q_1$, and $Q_2$ are each independently a hydrogen atom, a deuterium atom, a halogen atom, a hydroxyl group, a cyano group, an amino group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted anthryl group, a substituted or unsubstituted fluorenyl group, a substituted or unsubstituted carbazolyl group, or a substituted or unsubstituted pyridinyl group.

5. The heterocyclic compound as claimed in claim 1, wherein $R_1$ to $R_8$ are each independently a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted naphthyl group, a substituted or unsubstituted fluorenyl group, a substituted or unsubstituted phenanthrenyl group, a substituted or unsubstituted anthryl group, a substituted or unsubstituted triphenylenyl group, a substituted or unsubstituted pyrenyl group, a substituted or unsubstituted imidazolyl group, a substituted or unsubstituted benzoimidazolyl group, a substituted or unsubstituted pyridinyl group, a substituted or unsubstituted imidazopyridinyl group, a substituted or unsubstituted pyrimidinyl group, a substituted or unsubstituted imidazopyrimidinyl group, a substituted or unsubstituted indolyl group, a substituted or unsubstituted pyrido indolyl group, a substituted or unsubstituted carbazolyl group, a substituted or unsubstituted puranyl group, a substituted or unsubstituted benzopuranyl group, a substituted or unsubstituted dibenzopuranyl group, a substituted or unsubstituted thiophenyl group, a substituted or unsubstituted benzothiophenyl group, a substituted or unsubstituted dibenzothiophenyl group, a substituted or unsubstituted benzothiazolyl group, a substituted or unsubstituted benzooxazolyl group, a substituted or unsubstituted oxadiazolyl group, a substituted or unsubstituted triazinyl group, or a group represented by $N(Q_1)(Q_2)$, wherein $Q_1$, and $Q_2$ are each independently a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted naphthyl group, a substituted or unsubstituted fluorenyl group, a substituted or unsubstituted carbazolyl group, or a substituted or unsubstituted pyridinyl group.

6. The heterocyclic compound as claimed in claim 1, wherein $R_1$ and $R_5$ are each independently a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted naphthyl group, a substituted or unsubstituted fluorenyl group, a substituted or unsubstituted phenanthrenyl group, a substituted or unsubstituted anthryl group, a substituted or unsubstituted triphenylenyl group, a substituted or unsubstituted pyrenyl group, a substituted or unsubstituted imidazolyl group, a substituted or unsubstituted benzoimidazolyl group, a substituted or unsubstituted pyridinyl group, a substituted or unsubstituted imidazopyridinyl group, a substituted or unsubstituted pyrimidinyl group, a substituted or unsubstituted imidazopyrimidinyl group, a substituted or unsubstituted indolyl group, a substituted or unsubstituted pyrido indolyl group, a substituted or unsubstituted carbazolyl group, a substituted or unsubstituted puranyl group, a substituted or unsubstituted benzopuranyl group, a substituted or unsubstituted dibenzopuranyl group, a substituted or unsubstituted thiophenyl group, a substituted or unsubstituted benzothiophenyl group, a substituted or unsubstituted dibenzothiophenyl group, a substituted or unsubstituted benzothiazolyl group, a substituted or unsubstituted benzooxazolyl group, a substituted or unsubstituted oxadiazolyl group, a substituted or unsubstituted triazinyl group, or a group represented by $N(Q_1)(Q_2)$, wherein $Q_1$, and $Q_2$ are each independently a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a substituted or unsubstituted phenyl group, a substituted or unsubstituted naphthyl group, a substituted or unsubstituted fluorenyl group, a substituted or unsubstituted carbazolyl group, or a substituted or unsubstituted pyridinyl group, and $R_2$, $R_3$, $R_4$, $R_5$, $R_7$, and $R_8$ are each independently a hydrogen atom, a deuterium atom, a halogen atom, a substituted or unsubstituted methyl group, a substituted or unsubstituted ethyl group, a substituted or unsubstituted propyl group, a substituted or unsubstituted butyl group, or a substituted or unsubstituted pentyl.

7. The heterocyclic compound as claimed in claim 1, wherein:

$R_2$, $R_3$, $R_4$, $R_6$, $R_7$, and $R_8$ are hydrogen atoms, $R_1$ and $R_5$ are each independently a hydrogen atom, a deuterium atom, a halogen atom, a substituted or unsubstituted methyl group, a substituted or unsubstituted ethyl group, a substituted or unsubstituted propyl group, a substituted or unsubstituted isobutyl group, or a group represented by one of Formulae 4AA to 4BK below:

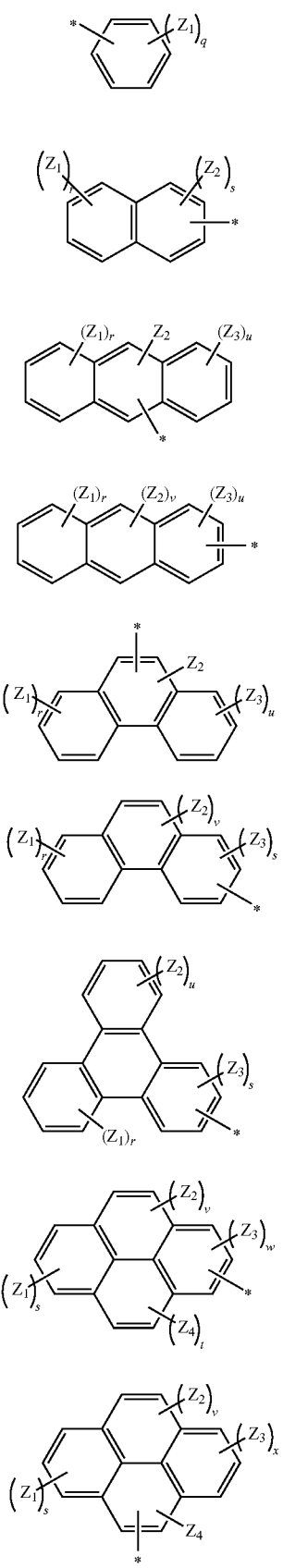
<Formula 4AA>
<Formula 4AB>
<Formula 4AC>
<Formula 4AD>
<Formula 4AE>
<Formula 4AF>
<Formula 4AG>
<Formula 4AH>
<Formula 4AI>
-continued
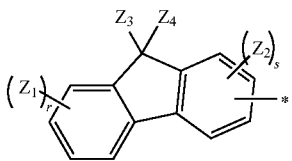
<Formula 4AJ>
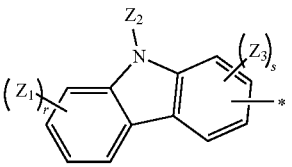
<Formula 4AK>
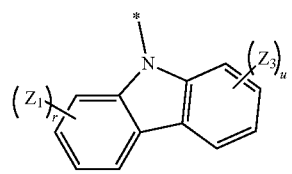
<Formula 4AL>
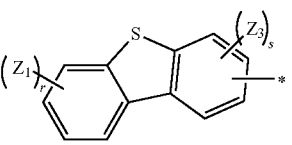
<Formula 4AM>
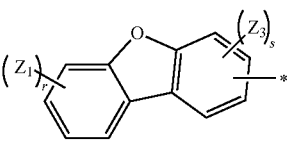
<Formula 4AN>
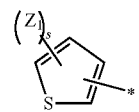
<Formula 4AO>
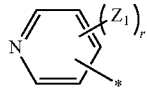
<Formula 4AP>
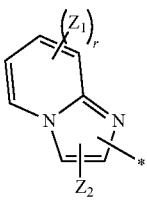
<Formula 4AQ>
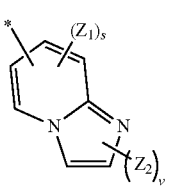
<Formula 4AR>

<Formula 4AS>
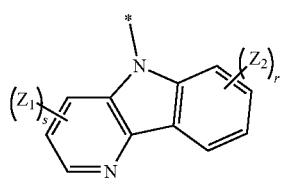
<Formula 4AT>
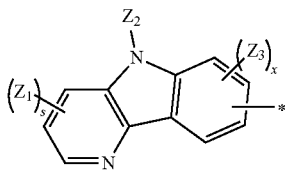
<Formula 4AU>
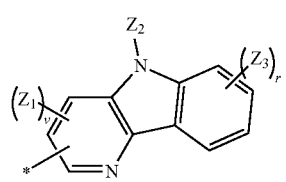
<Formula 4AV>
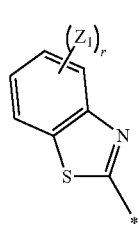
<Formula 4AW>
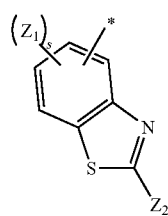
<Formula 4AX>
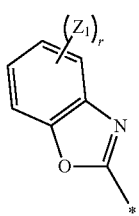
<Formula 4AY>
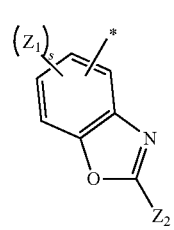
<Formula 4AZ>
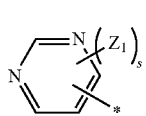
<Formula 4BA>
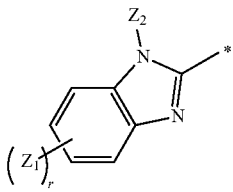
<Formula 4BB>
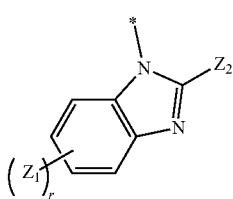
<Formula 4BC>
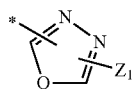
<Formula 4BD>
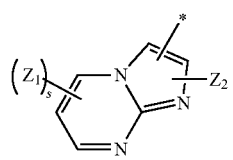
<Formula 4BE>
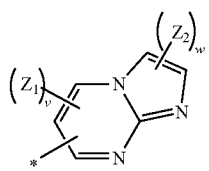
<Formula 4BF>
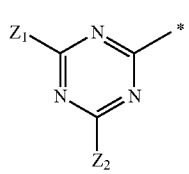
<Formula 4BG>
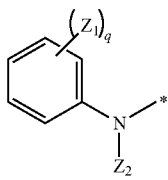
<Formula 4BH>
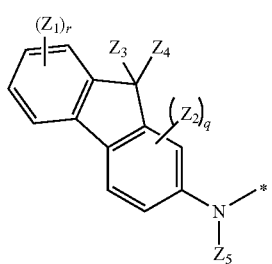

-continued

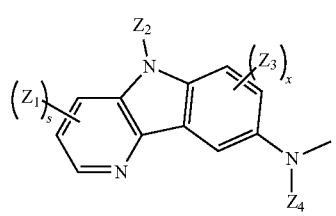
<Formula 4BI>

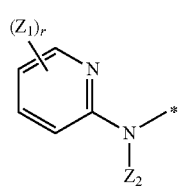
<Formula 4BJ>

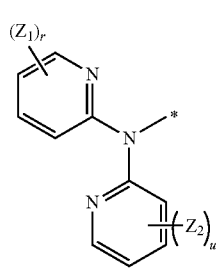
<Formula 4BK>

$Z_1$, $Z_2$, $Z_3$, $Z_4$, and $Z_5$ are each independently a hydrogen atom, a deuterium atom, a halogen atom, a hydroxy group, a cyano group, a trifluoromethyl group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, a substituted or unsubstituted anthryl group, or a substituted or unsubstituted pyridinyl group, q is an integer of 1 to 5, r and u are each independently an integer of 1 to 4, s and x are each independently an integer of 1 to 3, v is an integer of 1 or 2, and

* represents a binding site.

8. The heterocyclic compound as claimed in claim 1, wherein $L_1$ and $L_2$ are each independently a substituted or unsubstituted phenylene group, a substituted or unsubstituted naphthylene group, a substituted or unsubstituted anthrylene group, a substituted or unsubstituted phenanthrenylene group, a substituted or unsubstituted pyrenylene group, a substituted or unsubstituted chrysenylene group, a substituted or unsubstituted perylenylene group, a substituted or unsubstituted fluorenylene group, a substituted or unsubstituted spiro-fluorenyl group, a substituted or unsubstituted carbazolylene group, a substituted or unsubstituted pyridinylene group, a substituted or unsubstituted pyrimidinylene group, or a substituted or unsubstituted oxadiazolylene group.

9. The heterocyclic compound as claimed in claim 1, wherein:

$L_1$ and $L_2$ are each independently a group represented by one of Formulae 5A to 5I, below:

<Formula 5A>

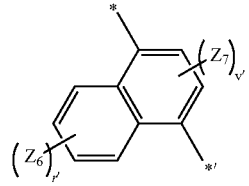
<Formula 5B>

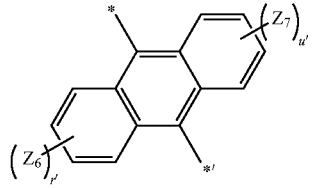
<Formula 5C>

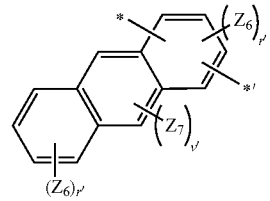
<Formula 5D>

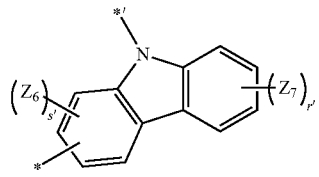
<Formula 5E>

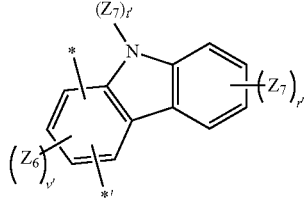
<Formula 5F>

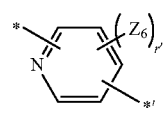
<Formula 5G>

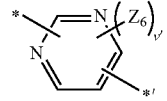
<Formula 5H>

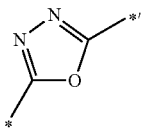
<Formula 5I>

$Z_6$, $Z_7$, and $Z_8$ are each independently a hydrogen atom, a deuterium atom, a halogen atom, a substituted or unsubstituted methyl group, a substituted or unsubstituted ethyl group, a substituted or unsubstituted propyl group, a substituted or unsubstituted butyl group, or a substituted or unsubstituted phenyl, r' and u' are each independently an integer of 1 to 4, s' is an integer of 1 to 3, v' and y' are each independently an integer of 1 to 2, and

* and *' each represent a binding site.

10. The heterocyclic compound as claimed in claim 1, wherein a and b are each independently an integer of 0 or 1.

11. The heterocyclic compound as claimed in claim 1, wherein the heterocyclic compound represented by Formula 1 is represented by one of the following Compounds 7, 10, 21, 24, 25, 31, 41, and 57:

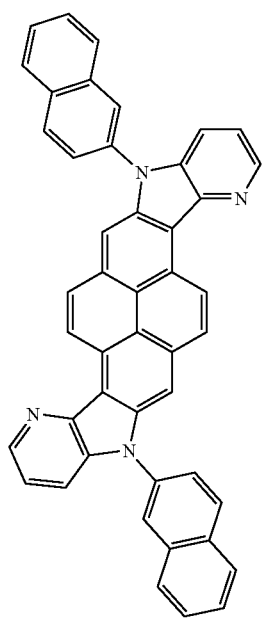

7

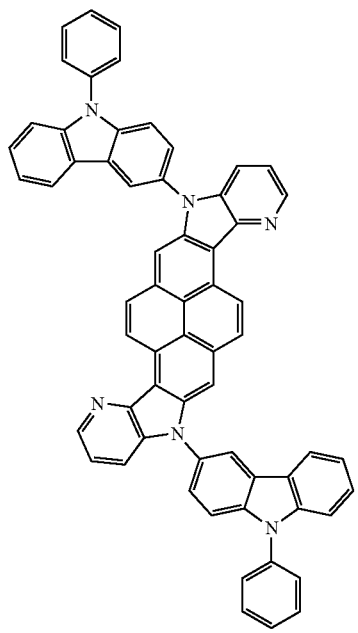

10

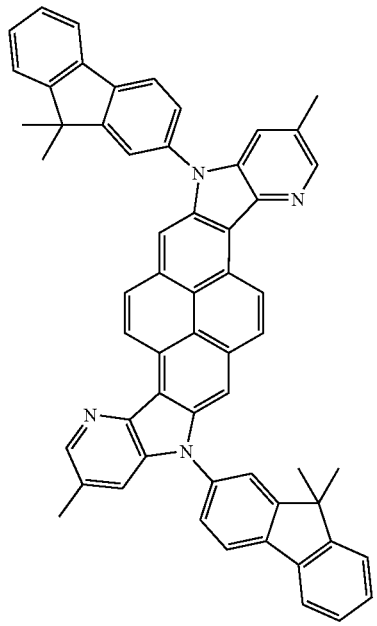

21

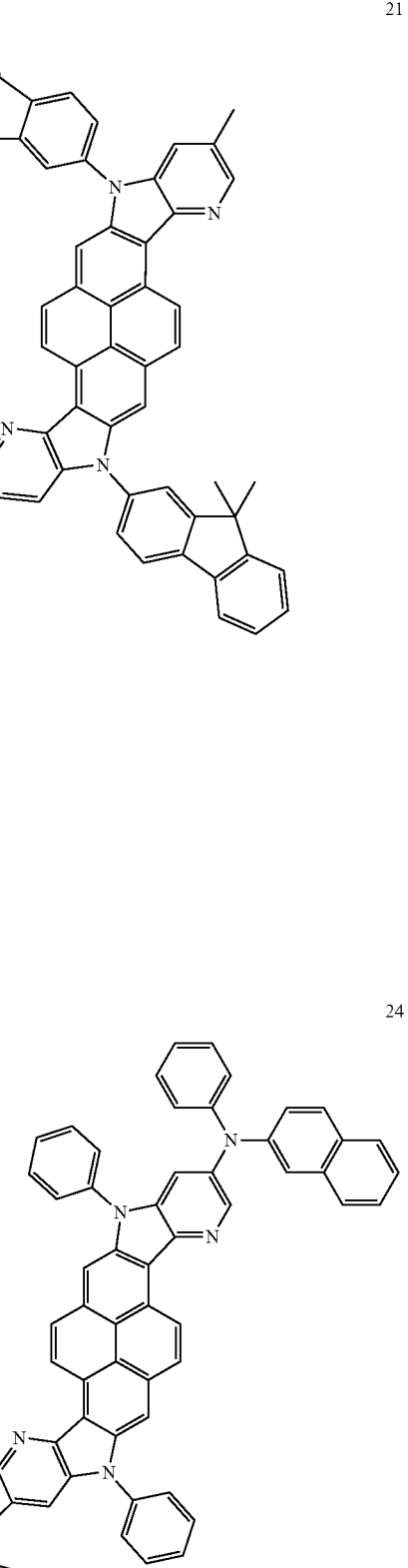

24

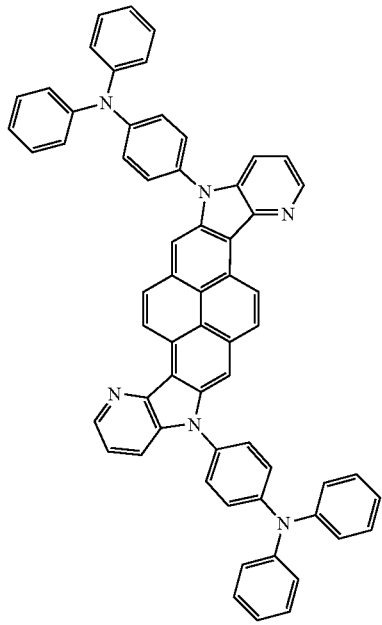

25

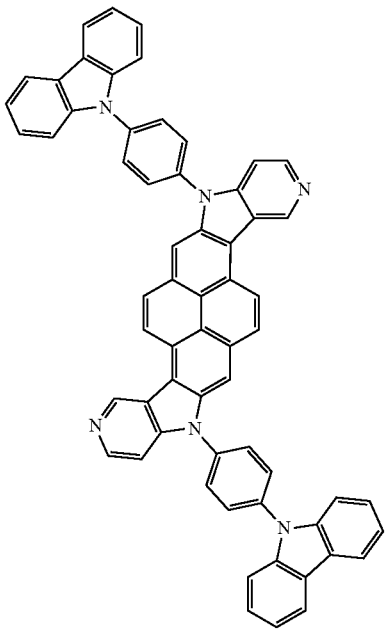
41

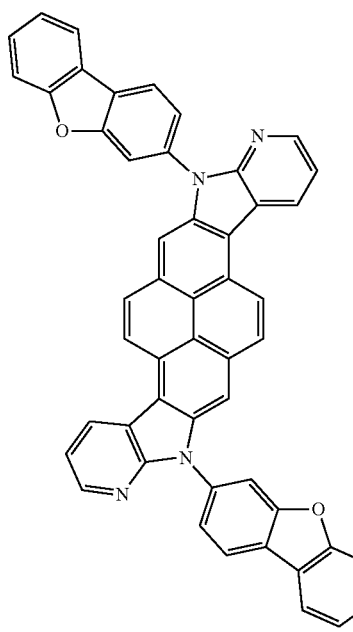
57

31

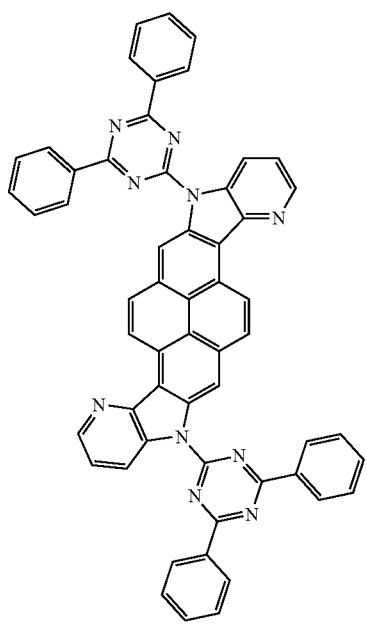

12. An organic light-emitting diode, comprising:
   a first electrode;
   a second electrode facing the first electrode; and
   a first layer between the first electrode and the second electrode, the first layer including the heterocyclic compound as claimed in claim 1 alone or in a mixed form with other materials.

13. The organic light-emitting diode as claimed in claim 12, wherein the first layer includes at least one layer selected from the group of a hole injection layer, a hole transport layer, a functional layer having a hole injection function and a hole transportation function, an electron blocking layer, an emission layer, a hole blocking layer, an electron transport layer, an electron injection layer, and a functional layer having an electron transportation function and an electron injection function.

14. The organic light-emitting diode as claimed in claim 12, wherein the first layer includes an emission layer, the emission layer including at least one selected from the group of a fluorescent host, a phosphorescent host, a fluorescent dopant, and a phosphorescent dopant.

15. The organic light-emitting diode as claimed in claim 14, wherein:
the emission layer includes the heterocyclic compound, and
  i) the fluorescent host includes the heterocyclic compound,
  ii) the fluorescent dopant includes the heterocyclic compound, or
  iii) the fluorescent host and the fluorescent dopant each include the heterocyclic compound.

16. The organic light-emitting diode as claimed in claim 12, wherein the first layer includes an emission layer, the emission layer including at least one selected from the group of an anthracene-based compound, an arylamine-based compound, and a styryl-based compound.

17. The organic light-emitting diode as claimed in claim 16, wherein the emission layer includes the heterocyclic compound.

18. The organic light-emitting diode as claimed in claim 12, wherein the first layer includes an electron transport layer, the electron transport layer including the heterocyclic compound.

19. The organic light-emitting diode as claimed in claim 12, wherein the first layer includes an electron transport layer, the electron transport layer including a metal-containing compound.

20. The organic light-emitting diode as claimed in claim 19, wherein the metal-containing compound includes a lithium (Li) complex.

21. The organic light-emitting diode as claimed in claim 12, wherein the first layer includes an emission layer and an electron transport layer, each of the emission layer and the electron transport layer including the heterocyclic compound.

22. The organic light-emitting diode as claimed in claim 12, wherein the first layer includes at least one layer selected from the group of a hole injection layer, a hole transport layer, and a functional layer having a hole injection function and a hole transportation function, the at least one layer selected from the group of the hole injection layer, the hole transport layer, and the functional layer having a hole injection function and a hole transportation function further including a charge generation material.

23. A flat display device, comprising:
a transistor including a source, a drain, a gate, and an active layer; and
the organic light-emitting diode as claimed in claim 12,
wherein the source or the drain is electrically connected to the first electrode of the organic light-emitting diode.

* * * * *